(12) United States Patent
Crienen et al.

(10) Patent No.: US 8,710,303 B2
(45) Date of Patent: Apr. 29, 2014

(54) CUCUMBER PLANTS WITH A COMPACT GROWING HABIT

(75) Inventors: Jack Crienen, Baarlo (NL); Gerhard T. M. Reuling, Heythuysen (NL); Bart Segers, GD Maasbree (NL); Marion Van de Wal, NX Best (NL)

(73) Assignee: Nunhems B.V., Nunhem (NL)

( * ) Notice: Subject to any disclaimer, the term of this patent is extended or adjusted under 35 U.S.C. 154(b) by 441 days.

(21) Appl. No.: 12/741,772

(22) PCT Filed: Nov. 7, 2008

(86) PCT No.: PCT/EP2008/009404
§ 371 (c)(1),
(2), (4) Date: Sep. 21, 2010

(87) PCT Pub. No.: WO2009/059777
PCT Pub. Date: May 14, 2009

(65) Prior Publication Data
US 2011/0047642 A1    Feb. 24, 2011

(51) Int. Cl.
*A01H 5/00* (2006.01)
*A01H 5/10* (2006.01)

(52) U.S. Cl.
USPC .......................................... 800/307; 800/299

(58) Field of Classification Search
None
See application file for complete search history.

(56) References Cited

U.S. PATENT DOCUMENTS 4,822,949 A    4/1989 Niego et al.

FOREIGN PATENT DOCUMENTS

| EP | 0534858 | 9/1992 |
| EP | 1317558 | 6/2003 |
| EP | 1433378 | 12/2003 |
| JP | 2004-095348 | 4/2001 |
| WO | WO 02/22836 | 3/2002 |

OTHER PUBLICATIONS

Xie et al (Cucurbit Gent. Coop. Rpt. vol. 24, pp. 110-136, 2001).*
Goode et al (Plant Variety Protection No. 008900073, Mar. 31, 1993).*
Xie and Wehner (2001) "Gene List 2001 for Cucumber," Gent Coop. Rpt. vol. 24, pp. 110-136 XP002483417.
Kauffman and Lower (1976) "Inheritance of an Extreme Dwarf Plant Type in Cucumber," Journal American Society Horticultural Science, vol. 101, No. 2, pp. 150-151 XP008092423.
Kubicki et al. (1986) "Induced Mutations in Cucumber ( cucumis stativus L.) V. Compact Type of Growth," Genetica Polonia, vol. 27, pp. 289-298 XP008092424.
De Lint et al. (1982) "Night Temperature and Number of Nodes and Flowering of the Main Stem of Glasshouse Cucumber *Cucumis sativus*." Netherlands Journal of Agricultural Science, vol. 30, No. 3, pp. 149-160 XP008092421.
Xiong Jinqiao et al. (2002) "Effect of DIF and end-of-day Light Quality on Stem Elongation in *Cucumis sativus*," XP002483418.
M.J. Goode et al., Arkansas Little Leaf, Plant Variety Protection No. 008900073, Received: 1989.
Boonekamp, Hogedraadteelt Komkommer, Groeten & Fruit, Week 31 (2006).
Goode, et al., "Little-Leaf, A New Kind of Pickling Cucumber Plant, Arkansas Farm Research," p. 4 (1980).
Schultheis, et al., "Optimum Planting Density and Harvest Stage for Little-Leaf and Normal-Leaf Cucumber for Once-Over Harvest," Can. J. Plant Sci., 78:333-340 (1998).
Wehner, Inheritance of Littleleaf and Multi-Branched Plant Type in Cucumber (1987).
Gemes-Juhasz, et al. "Effect of optimal stage of female gametophyte and heat treatment on in vitro gynogensis induction in cucumber (*Cucumis sativus* L.)," Plant Cell Rep, vol. 21, pp. 105-111; 2002.
Honkoop, Erik; "Planmatig telen helpt hoge draad komkommer vooruit weer in beeld;" Editors GFActueel; Sep. 21, 2007.
Scheffe, Henry, "A method for udging all contrasts in the analysis of variance," Biometrika, vol. 40, No. ½; 87-104; Jun. 1953.
Scheffe, Henry, "The analysis of variance," John Wiley, New York; 1959 [Table of Contents].
van Steekelenburg, "Didymella bryoniae on glasshouse cucumbers," dissertation: p. 105, Wageningen Agricultural University: N.A.M.: 1986.
Vos, Pieter, et al. "AFLP; a new technique for DNA fingerprint," Oxford University Press, Nucleic Acids Research, vol. 23, No. 21, pp. 4407-4414, 1995.
Schultheis, Jonathan R., et al. "Optimum planting density and harvest stage for little-leaf and normal-leaf cucumber for one-over harvest," Canadian Journal of Plant Science, vol. 78, pp. 333-340; 1998.
Boonekamp, Gerard; "Hogedraadtecht komkommer," Groenten & Fruit, week 31, pp. 18-19; 2006.
"CPVO Protocol"; Protocol for Distinctness, Uniformity and Stability Test, Cucumber, *Cucumis sativus* L. European Union, Community Plant Variety Office, Boulevard Marechal Foch, FR—49021, Angers Cedex 02, Document CPVO-TP/61/1 (2008).

* cited by examiner

*Primary Examiner* — Shubo (Joe) Zhou
*Assistant Examiner* — Keith Robinson
(74) *Attorney, Agent, or Firm* — Hunton & Williams LLP

(57) ABSTRACT

The invention relates to the breeding of cucumbers, and especially to a new cucumber plant with a valuable new characteristic. This new characteristic leads to an improvement in the growth properties and so to a simplification and improvement of cucumber cultivation. Seeds according to the invention and methods for introducing the new characteristic into other cucumber plants are also covered. Self-pollination and cross-pollination of the plants according to the invention are described, as well as the production of doubled haploids from these plants.

18 Claims, 3 Drawing Sheets

```
                            SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: primer E17

<400> SEQUENCE: 1
```

```
gactgcgtac caattccg                                                    18

<210> SEQ ID NO 2
<211> LENGTH: 18
<212> TYPE: DNA
<213> ORGANISM: Artificial Sequence
<220> FEATURE:
<223> OTHER INFORMATION: primer E24

<400> SEQUENCE: 2
gactgcgtac caattctc                                                    18

<210> SEQ ID NO 3
<211> LENGTH: 18
<212> TYPE: DNA
<213> ORGANISM: Artificial Sequence
<220> FEATURE:
<223> OTHER INFORMATION: primer E14

<400> SEQUENCE: 3
gactgcgtac caattcat                                                    18

<210> SEQ ID NO 4
<211> LENGTH: 18
<212> TYPE: DNA
<213> ORGANISM: Artificial Sequence
<220> FEATURE:
<223> OTHER INFORMATION: primer E19

<400> SEQUENCE: 4
gactgcgtac caattcga                                                    18

<210> SEQ ID NO 5
<211> LENGTH: 18
<212> TYPE: DNA
<213> ORGANISM: Artificial Sequence
<220> FEATURE:
<223> OTHER INFORMATION: primer E16

<400> SEQUENCE: 5
gactgcgtac caattccc                                                    18

<210> SEQ ID NO 6
<211> LENGTH: 19
<212> TYPE: DNA
<213> ORGANISM: Artificial Sequence
<220> FEATURE:
<223> OTHER INFORMATION: primer M54

<400> SEQUENCE: 6
gatgagtcct gagtaacct                                                   19

<210> SEQ ID NO 7
<211> LENGTH: 19
<212> TYPE: DNA
<213> ORGANISM: Artificial Sequence
<220> FEATURE:
<223> OTHER INFORMATION: primer M49

<400> SEQUENCE: 7
gatgagtcct gagtaacag                                                   19

<210> SEQ ID NO 8
<211> LENGTH: 19
<212> TYPE: DNA
<213> ORGANISM: Artificial Sequence
<220> FEATURE:
```

<223> OTHER INFORMATION: primer M61

<400> SEQUENCE: 8
gatgagtcct gagtaactg                                                    19

<210> SEQ ID NO 9
<211> LENGTH: 19
<212> TYPE: DNA
<213> ORGANISM: Artificial Sequence
<220> FEATURE:
<223> OTHER INFORMATION: primer M50

<400> SEQUENCE: 9
gatgagtcct gagtaacat                                                    19

<210> SEQ ID NO 10
<211> LENGTH: 19
<212> TYPE: DNA
<213> ORGANISM: Artificial Sequence
<220> FEATURE:
<223> OTHER INFORMATION: primer M47

<400> SEQUENCE: 10
gatgagtcct gagtaacaa                                                    19

<210> SEQ ID NO 11
<211> LENGTH: 24
<212> TYPE: DNA
<213> ORGANISM: Artificial Sequence
<220> FEATURE:
<223> OTHER INFORMATION: MAS4-f primer

<400> SEQUENCE: 11
gcatgcatgg actgacttac taga                                              24

<210> SEQ ID NO 12
<211> LENGTH: 26
<212> TYPE: DNA
<213> ORGANISM: Artificial Sequence
<220> FEATURE:
<223> OTHER INFORMATION: MAS4-r primer

<400> SEQUENCE: 12
ggagactcac atatctttct gacaca                                            26

<210> SEQ ID NO 13
<211> LENGTH: 19
<212> TYPE: DNA
<213> ORGANISM: Artificial Sequence
<220> FEATURE:
<223> OTHER INFORMATION: MAS4 - VIC probe

<400> SEQUENCE: 13
ctaactgcaa aaacaatgt                                                    19

<210> SEQ ID NO 14
<211> LENGTH: 17
<212> TYPE: DNA
<213> ORGANISM: Artificial Sequence
<220> FEATURE:
<223> OTHER INFORMATION: MAS4 - FAM probe

<400> SEQUENCE: 14
aactgcaaaa gcaatgt                                                      17

<210> SEQ ID NO 15

```
<211> LENGTH: 25
<212> TYPE: DNA
<213> ORGANISM: Artificial Sequence
<220> FEATURE:
<223> OTHER INFORMATION: MAS37-f primer

<400> SEQUENCE: 15
aggatcacct gatgttcaag gagta                                              25

<210> SEQ ID NO 16
<211> LENGTH: 24
<212> TYPE: DNA
<213> ORGANISM: Artificial Sequence
<220> FEATURE:
<223> OTHER INFORMATION: MAS37-r primer

<400> SEQUENCE: 16
cgatgataca gttggaagga tgga                                               24

<210> SEQ ID NO 17
<211> LENGTH: 20
<212> TYPE: DNA
<213> ORGANISM: Artificial Sequence
<220> FEATURE:
<223> OTHER INFORMATION: MAS37 - VIC probe

<400> SEQUENCE: 17
tatggacgac tttcatgtag                                                    20

<210> SEQ ID NO 18
<211> LENGTH: 18
<212> TYPE: DNA
<213> ORGANISM: Artificial Sequence
<220> FEATURE:
<223> OTHER INFORMATION: MAS37 - FAM probe

<400> SEQUENCE: 18
tggacgactt tgatgtag                                                      18
```

CUCUMBER PLANTS WITH A COMPACT GROWING HABIT

CROSS-REFERENCE TO RELATED APPLICATIONS

This application is the U.S. National Stage filing of International Application No. PCT/EP2008/009404, filed Nov. 7, 2008, which claims priority to NL 2000992, filed Nov. 9, 2007, the disclosures of both of which are hereby incorporated by reference.

FIELD OF THE INVENTION

The present invention relates to the modification of the cucumber genome, which comes to expression as a new characteristic of cucumber plants, especially *Cucumis sativus* spp. *sativus*, more particularly the long cucumber type, and above all the Dutch cucumber, but the present invention can also be used for all kinds and types of cucumber plants, such as gherkins, short cucumbers, long cucumbers, slicer cucumbers and the like. Plants according to the invention are preferably indeterminate, rather than determinate, and are not dwarf types. This new plant type needs less labour-intensive cultivation in the production of cucumbers while providing more fruits per plant. In one of the embodiments of the invention a higher plant density can be obtained in the cultivation of the cucumber. The plants according to the invention are very suitable for the system of high-wire cultivation, which is gaining ground in the standard cultivation of the cucumber (Boonekamp, 2006; Honkoop, 2006). The more compact and more open type of cucumber plants according to the invention is a great advantage in high-wire cultivation and/or mechanical harvest of fruit. In a specific embodiment of the present invention, the new compact cucumber plants have, in comparison with the usual type of long cucumber (such as the reference varieties Korinda or Sabrina), shorter internodes (and a shorter stem length per 15 internodes), shorter lateral shoots, smaller and darker leaves which remain green for longer, less "bumpy" leaves (flatter), smaller flowers, a more horizontal orientation of the leaves, shorter fruits, and above all a slower growth rate. This new combination of characteristics is very valuable for the development of commercial cucumber varieties, especially long, indeterminate cucumbers. These characteristics are statistically significantly different from the normal long cucumber type in cucumber plants heterozygous and homozygous for the gene conferring the characteristics, referred to herein as the "compact gene". These characteristics are due to the expression of a single genetic locus, with monogenic intermediate heredity, i.e. the characteristics are more pronounced in the homozygous plant than in the heterozygous plant where they give an 'intermediate' phenotype. This genetic locus can be demonstrated and monitored with the aid of flanking AFLP markers in the descendants obtained by hybridizing a cucumber plant that comprises this genetic locus with a short cucumber type or a gherkin type plant that does not contain this genetic locus, and the genetic locus in question can be introduced, by hybridization, into every plant that can be hybridized with a cucumber plant according to the present invention, optionally after embryo rescue and/or the use of other methods employed to obtain hybrids with these or related species, such as plants of the *Cucumis sativus* species. Thus, both phenotypic selection (of the characteristics conferred by the compact gene) and/or molecular marker selection can be used to detect and/or transfer the compact gene to plants of the species *Cucumis sativus* and to generate plants with a homozygous compact or heterozygous (intermediate) compact phenotype. The gene can be introduced into any cucumber variety or breeding line, in one embodiment especially long cucumber varieties or lines, and its expression can thus change the variety's/line's phenotype from a fast growing, closed plant into a slow growing plant having the compact characteristics conferred by the gene. This gene, therefore, opens up the possibility to cultivate long cucumber varieties in high-wire cultivation, reducing cost and labour, and increasing plant density and fruit yield. Cucumber plants according to the invention are preferably indeterminate, as fruits can then be harvested over a long period.

COMPARISON WITH THE PRIOR ART

The usual, cultivated cucumber plant (*Cucumis sativus* L.) has been developed from the original wild gherkin/cucumber plant by plant breeding and is phenotypically essentially identical to the latter. Plant breeding has produced our common cucumber type, which only has female flowers. The cucumber fruit grows without any kind of pollination or fertilization, so it is parthenocarpic. The common cucumber fruits, which are intended for use by the consumer as a vegetable, only contain some thin and loose seeds. Gherkins, long cucumbers, short cucumbers, mini-cucumbers, snack cucumbers, Beith Alpha cucumbers and slicer cucumbers all belong to the species *Cucumis sativus*. Courgettes, melons, pumpkins and patissons (custard marrows) all belong to the family of cucumber-type plants or *Cucurbitaceae*, together with the cucumber itself. Most of the current cucumber varieties are hybrids (F1), obtained by crossing two genetically different parent lines.

The cultivation of the cucumber is a very intensive farming operation that calls for a great deal of care and labour if the best yield is to be obtained. In the Netherlands, Canada and the surrounding countries its cultivation proceeds throughout the year, mainly in greenhouses. In order to ensure a high yield of the fruit, the surplus leaves must be removed in good time, so that no energy is lost in superfluous vegetative growth, and the plant is kept sufficiently open to facilitate work on it. Furthermore, an open plant improves the quality of the fruit. However, a sufficient number of leaves must be kept to ensure optimum photosynthesis, evaporation and respiration in the plant.

The usual type of cucumber plant producing the customary long cucumber type exhibits little variation in its characteristics, namely in the rate of growth, length of the lateral shoots, size of the leaves, colour of the leaves, retention of the green colour by the leaves, internodal length, size of the flowers, length of the fruits and their rate of growth. Table 1 provides typical characteristics of the plants, leaves, flowers and fruits in the greenhouse, here for the long cucumber type cultivar Korinda.

In the customary (traditional) method used currently for the cultivation of cucumbers in greenhouses, the main stem of the plant is led up to a horizontal iron wire that is suspended at a height of about two meters above the ground. When the plant reaches this height and attaches to the wire, it is "topped" by removing its growth point in order to terminate further proliferation, whereupon lateral shoots start to develop. These lateral shoots are allowed to grow downward to a height of about 1 meter above the ground, and the growth points are then removed from them. This is followed by flowering and the development of the fruits both on the stem and on the lateral shoots or tendrils, but the fruits on the tendrils develop later than those on the stem. The fruits are harvested about 6 weeks after sowing. This is known as the traditional method of cultivation.

During the period of cultivation, the plants need intensive care in the form of correct fertilization, irrigation, climate control, disease control and the removal of excess, yellow or dead leaves in order to ensure the best yield and a high quality for the produce. The growth conditions of the plants are, thus, fully controlled, reducing the impact of environmental factors on the plant phenotype. Owing to this intensive work and the expensive greenhouses used, this is a relatively costly cultivation method. Ways are, therefore, constantly sought to reduce the work and raise and accelerate the production of cucumbers in such a way that the quality of the fruit is retained or even improved. In one attempt, for example, no lateral tendrils are allowed to grow and all the harvest comes from the stem. This approach, called high-wire cultivation, needs less work and gives a higher yield of qualitatively better produce. However, the current varieties are not very suitable for this method, because they grow too long, owing to their rapid growth and long internodes. The compact nature of the plants described herein makes it possible to develop cucumber plants or varieties that are more suitable for this type of new cultivation. Another development concerns the use of harvesting robots, such as the existing ones devised by the GreenVision Service at the University and Research Centre of Wageningen in the Netherlands (see http://www.greenvision.wur.nl/). Since the new compact plants according to the invention have smaller, horizontal leaves, their fruits are more visible and easier to pick by these robots than in the case of the usual type of plant, which considerably raises the yield when a harvesting robot is used.

Furthermore, cucumbers comprising the compact gene according to the invention, preferably in the heterozygous form (having an intermediate compact phenotype), can be planted with a higher stem density, either by having more plants per $m^2$ at the outset, or by later allowing more stems to develop during cultivation, as is well known in the field of cucumber production. In the high-wire cultivation of long cucumbers in the Netherlands, a stem density of around 2.6-2.8 plants per $m^2$ then becomes possible under ideal conditions, as compared to a stem density of about 2.2 plants (or stems) per $m^2$ in the current high-wire cultivation of long cucumbers in the Netherlands under ideal conditions. Thus, in one embodiment of the invention, cucumber plants according to the invention are grown at a stem density of more than 2.2 plants (or stems) per $m^2$, preferably at least 2.4, 2.5, 2.6. 2.7, 2.8, 2.9 or 3.0 plants (or stems) per $m^2$, or more; more preferably about 2.6-2.8 stems per $m^2$. In one form of the invention, at least about 20%, preferably at least about 22%, 23% or 24% more stems per $m^2$ can be used in high-wire cultivation in the case of the more compact plants (compared to the traditional cucumber lacking the compact gene according to the invention, such as Korinda or Sabrina), such as plants that are heterozygous for the compact gene according to the invention.

In the prior art, a type of gherkin (pickling cucumber) is cultivated outdoors that has small leaves with a greater number of lateral shoots per plant (multiple branching), this plant having been identified in Arkansas and designated as H-19 or Arkansas Little Leaf (US Plant Variety Protection No. 8900073). It has been established that the phenotype of the smaller leaves of these short gherkin plants is due to a single recessive gene (Wehner et al., 1987; Goode et al., 1980). This phenotype is not available for the cultivation of the usual long Dutch cucumber. Since a recessive gene is involved here, no intermediate forms of this phenotype are possible, unlike in the case of the plants according to the present invention. The fruit quality of these little-leaf cucumbers has been found to be inferior to the lines tested, which had normal leaves (Schultheis et al., 1998). Also, plants according to the invention are not multi branching as seen in Little Leaf.

Also so-called "compact" cucumber plants have been described in the prior art, comprising either the mutation cp or cp2 (Kauffman and Lower, 1976 and Kubicki et al., 1986). Despite the same name, these two gene mutations are both at different loci in the genome than the present compact gene and express different characteristics than the compact gene of the instant invention. In contrast to the present compact gene, which is monogenic intermediate (expressing a compact phenotype when homozygous but an intermediate compact phenotype when heterozygous (see Table 1, heterozygous plant type), cp and cp2 are homozygous recessive, expressing shorter internodes only when two copies of the mutant allele are present and having a 'normal' phenotype when the mutant allele is in heterozygous form. Heterozygotes of the compact gene of the instant invention are, thus, phenotypically very different from heterozygotes of cp or cp2: heterozygotes of cp or cp2 display a normal (non-compact or wild-type) phenotype. The cp2 mutant has been described to produce 'intermediate forms', but only when homozygous (cp2/cp2) and only in interaction with another mutation called bu (bushy). In addition, when comparing the characteristics of the homozygous compact plants according to the invention and the homozygous cp or cp2 plants, these differ in their phenotypic characteristics. Homozygous cp2/cp2 plants have a main vine length of less than 50 cm (15-35 cm), and represent thus dwarf types, not suitable for traditional or high-wire cultivation, which needs much longer stems (preferably more than 100 cm at 50 days after sowing, under standard Dutch summer greenhouse conditions for the continuous production of fruit. Homozygous cp/cp plants are "extreme dwarf" plants (having a stem length of less than 35 cm), also not suitable for traditional or high-wire cultivation. The cp mutation also is associated with negative effects, such as reduced fruit quality (lighter color, somewhat smaller fruit, larger seed cavities than acceptable commercial cultivars lacking the cp mutation (see Kauffman and Lower, 1976, page 151, last paragraph).

Standard Dutch summer greenhouse conditions, or Dutch summer greenhouse conditions, are those ordinarily used by Dutch cucumber breeders in the summer. Evidently there can be variations in these conditions according to the preference of the breeder, the investments made, the resources available etc., but such variations have no effect on the compact gene characteristics which will always be clearly identified using the methods and/or markers described herein. In one embodiment of the invention, Standard Dutch summer greenhouse conditions as used herein are:

After sowing (the 4th of July) in vermiculite at 28° C., plants are transplanted in rockwool blocks in a nursery with usual 13-17 plts/m2, with a temperature of about 21° C.

About 21-23 days after sowing, the blocks are planted in a Dutch glasshouse on rockwool slabs, where water and nutrients are added by dripping. The EC of the water is about 2.0 (mS/m) with a pH of about 5.5. Depending on the weather conditions, the EC can be increased up to 3.0. In Dutch situations, these conditions can vary from grower to grower. The temperature in the greenhouse is preferably fixed on a temperature of about 21° C. during the day and 18-18.5° C. during the night. Due to higher radiation the temperature may rise, but preferably not higher than 28° C. (by ventilation, by watercooling on the roof glass or by shading with screens). Plant density is preferably about 1.4 plants/m2.

Plants are winded around a vertical robe to a horizontal wire at about 2.0-2.2 m height. There the plants are topped and 2 laterals will grow from the top downwards. Standard all laterals are removed from the mainstem except the last 2 or 3 laterals.

The first 4-5 axils will be made free of fruits. In the next axils preferably 1 fruit will be continued to develop to a mature fruit. In the top of the plant just below the wire, sometimes growers will keep up to 3 nodes with 2 fruits in the axil.

After harvesting mature fruits of about 400-450 grams on the mainstem, growers continue to harvest fruits on the lateral shoots.

Under the conditions mentioned above, plants will start to produce 16-19 days after transplanting in the greenhouse on the slabs.

Whether the compact gene is the same as another gene conferring the same plurality of characteristics (which is unlikely to exist) can be established by checking for allelism of the trait. For example, two phenotypically similar or identical plants (e.g., one with the compact gene and one wherein the presence of the compact gene is to be tested) are crossed and the F1 and/or F2 progeny are analyzed for segregation of the characteristics. Alternatively, the inheritance of the gene to be tested is determined by looking at the progeny and determining Mendelian segregation of the phenotype. A gene which inherits recessively cannot be the same as a gene which inherits in an intermediate way or a gene with dominant inheritance.

It is noted that none of the cucumber plants (long, short, gherkin type, etc.) comprising the compact gene according to the invention are "dwarf" plants (which would not be suitable for traditional or high wire cultivation), but are plants which are still tall compared to the same plant lacking the compact gene according to the invention, i.e. the compact plants according to the invention are much taller than "dwarf" plants. "Dwarf" plants, as used herein, are defined as having a main stem of less than 50 cm during their entire life cycle, and therefore, also at 50 days after sowing in normal growing conditions. Kauffman and Lower (1979, lines 2-5) state that compact determinate plants are 12 cm or less at 8 weeks. In contrast, the plants according to the invention are not "dwarf" plants and comprise a stem length of more than 50 cm, preferably more than 70 cm, 80 cm, 90 cm or 100 cm at 50 days after sowing, when grown under standard greenhouse conditions, such as Dutch summer greenhouse conditions. Height can also be measured and compared at 15 internodes when grown under the same conditions (e.g. Dutch summer greenhouse conditions as described in the Examples), whereby plants according to the invention are much taller than cp or cp2 plants and comprise a stem length at 15 internodes (as measured from the substrate) of more than 50 cm, preferably more than 80, 90 or 100 cm. See also Table 1, wherein the mean values for the stem length at 15 internodes for the cucumber plants was: 147 cm for the normal cucumber plants, 126 cm for the heterozygous compact plants and 109 cm for the homozygous compact plants (74% of the value for normal plants).

SUMMARY OF THE INVENTION

The present invention relates to cucumber plants that comprise the compact gene in their genome, either in homozygous or in heterozygous form, in which case the expression of this (homozygous or heterozygous) compact gene ensures that these plants differ from the usual type of cucumber plants, such as the usual long cucumber type (e.g. cultivar Korinda or Sabrina), by exhibiting a combination of the following phenotypical characteristics when grown under the same conditions (e.g. Dutch summer greenhouse conditions): shorter lateral shoots, shorter internodes, smaller leaves, smaller flowers, shorter fruits, and especially a slower rate of growth, shorter lateral shoots, shorter internodes, smaller and more brittle leaves, leaves that are a darker green colour and are less "bumpy" (less tuberculate), a more horizontal foliage, smaller flowers, and shorter fruits that weigh less (see also Table 1). According to one of the embodiments, these plants with the compact gene are of the long cucumber type, such as hybrid long cucumber plants comprising the compact gene in heterozygous form. Such a hybrid is, for example, produced by crossing two preferably homozygous parent lines, for example a normal long cucumber line or variety (lacking the compact gene) with a plant according to the invention comprising the compact gene in homozygous form. The compact gene can also be introduced into plants lacking the compact gene by crossing such a plant with a plant having the compact gene in heterozygous form and selecting hybrid progeny comprising the compact gene (using phenotypic and/or marker selection as described elsewhere herein). See also Table 1 for mean phenotypic differences between normal cucumber (long type), heterozygous compact and homozygous compact plants.

One form of the invention relates to one of the above cucumber plants in which the compact gene imparts the following characteristics: a) in the case of the plants with the compact gene in the homozygous state, the area of the leaf blade of the tenth true leaf 39 or 35 days after sowing is at most 50%, preferably at most 40%, of the area of the leaf blade of cucumber plants of the usual type of cucumber (e.g. cultivar Korinda) 39 or 35 days after sowing, b) in the case of plants with the compact gene in the homozygous state, the maximum width of the petals 39 or 45 days after sowing is at most 75%, preferably at most 70%, of the maximum width of the petals of the usual type of cucumber 39 or 45 days after sowing, c) in the case of plants with the compact gene in the homozygous state, the length of the lateral shoots 56 days after sowing is at most 60%, preferably at most 50%, of the length of the lateral shoots 56 days after sowing the usual type of cucumber plant, and d) in the case of plants with the compact gene in the homozygous state, the number of internodes on the lateral shoots 56 days after sowing is at most 70%, preferably at most 60%, of the number of internodes on the lateral shoots 56 days after sowing the usual type of cucumber plants.

One form of the invention relates to one of the above cucumber plants in which the compact gene imparts the following characteristics: a) in the case of the plants with the compact gene in the homozygous state, the stem length at 15 internodes (at e.g. about 56 days after sowing) is at most 85%, preferably at most 80% or 75%, of the stem length of cucumber plants of the usual type of cucumber (e.g. cultivar Korinda) (at e.g. 56 days after sowing), b) in the case of plants with the compact gene in the homozygous state, the leaf width (at e.g. 35 days after sowing) is at most 70%, preferably at most 60%, of the leaf width of the usual type of cucumber (at e.g. 35 days after sowing) and c) in case of plants with the compact gene in the homozygous state, the leaf length (at e.g. 35 days after sowing) is at most 75%, preferably at most 70% or 65%, of the leaf length of the usual type of cucumber (at e.g. 35 days after sowing).

In another embodiment of the invention, cucumber plants, preferably long type cucumber plants, are provided which comprise the compact gene in heterozygous form and comprise the following combination (complex) of compact characteristics (based on mean values of at least about 10 or more plants and compared to control plants grown at the same time under the same conditions): the mean stem length from the substrate up to the 15$^{th}$ internode is equal to or less than 95%, preferably equal to or less than 90% or 88% of the mean stem length of a normal (e.g. long) cucumber plant lacking the compact gene; the mean internode length is equal to or less than 90%, more preferably equal to or less than 85% of the mean internode length of the normal (e.g. long) cucumber plant lacking the compact gene; the mean leaf length is equal to or less than 95%, preferably 93% or 91% of the normal (e.g. long) cucumber plant; the mean leaf width is equal to or less than 90%, preferably 88 or 87% of the normal (e.g. long) cucumber plant lacking the compact gene; the mean leaf blade area is equal to or less than 90%, preferably 85 or 80% of the normal (e.g. long) cucumber plant lacking the compact gene. In addition to the above the plants according to the invention comprising the compact gene in heterozygous form may comprise the following characteristics: the orientation of the leaves is more horizontal than in the normal (e.g. long) cucumber type, having a score of at least 4, preferably 4.5 or more on a scale of 1-9, with 1 being hanging down vertically and 9 being horizontal; the leaf color is darker than in the normal (e.g. long) cucumber type, having a score of at least 5, preferably at least 6, 6.5 or 7 on a scale of 1-9, with 1 being light and 9 being dark green; leaf color can also be determined by measuring chlorophyll content as described in the examples (the mean leaf chlorophyll content of leaves obtained from a plant having the compact gene in heterozygous form is higher than in the normal cucumber type and has a concentration of 3.000 (three thousand) µg/gram or more using ethanol extraction as described in the examples, i.e. a concentration of at least 105%, preferably at least 108%, 110%, more preferably at least 115%, 120% or 130% of the chlorophyll concentration of leaves of the same age and grown under the same conditions but lacking the compact gene); flowers are smaller, in that the length of the petals is equal to or less than 85%, preferably 82%, more preferably 80% of the petals of the normal (e.g., long) cucumber type lacking the compact gene and the petal width is equal to or less than 80%, preferably 75%, 74% or 70% of the petal width of the normal (e.g., long) cucumber type; fruit length is also reduced compared to the normal (e.g., long) cucumber type, having a length which is equal to or less than 95%, preferably 90%, more preferably 89% of the normal (e.g. long) cucumber fruit lacking the compact gene.

Also seeds, harvested fruit and plant parts (cell or tissue cultures, pollen, flowers, etc.) of such plants are provided herein. In one embodiment plants with the above intermediate compact characteristics are derived from seeds deposited under NCIMB Accession number 41266 (long type cucumber, homozygous for the compact gene), by crossing a plant grown from such seeds (or a plant derived therefrom, e.g. by selfing) with a long type cucumber plant lacking the compact gene and collecting the hybrid seeds from said cross. It is understood that many different crosses and/or selfings can be done to introduce the compact gene in heterozygous form into a long type cucumber plant to generate a hybrid comprising the compact gene in heterozygous form and having an 'intermediate compact' phenotype and good agronomic characteristics. Any such hybrid is encompassed herein. Selection of hybrids comprising the compact gene in heterozygous form can be done either phenotypically (based on the phenotypic compact characteristics) and/or using molecular markers, such as AFLP markers described herein or derived from the markers described or other AFLP markers polymorphic between a cucumber plant lacking the compact gene and a cucumber plant comprising the compact gene, which are linked to the compact gene. The AFLP markers disclosed in the present application are not polymorphic in long cucumber types, so that selection of a long cucumber type comprising the compact gene in heterozygous form involves crossing such a plant (or a plant suspected to be heterozygous) with a short cucumber or gherkin (both lacking the compact gene) and analyzing the progeny of such cross (e.g. the F1 and/or F2 generation) with one or more AFLP markers linked to the compact locus and/or markers derived from these. Such an analysis can thus be used to verify that the compact gene is present in heterozygous form in the long cucumber used as parent in the cross with the short cucumber or gherkin.

A marker "derived" from an AFLP marker according to the invention is a molecular marker which is still coupled to the compact gene locus and which is found in a flanking region of within 5 kb, preferably within 4, 3, 2, 1, 0.5 kb, or less, from the original AFLP marker or within the original AFLP marker sequence itself. A derived marker may, thus, be developed using the original AFLP marker and/or the sequence of the original AFLP marker of the invention. For example, the AFLP marker can be sequenced (e.g. the DNA marker band can be obtained from the gel and sequenced) and a polymorphism can be identified with the AFLP marker sequence or flanking the AFLP marker sequence on either side (e.g. within about 1, 2, 3, 4 or 5 kb from the original AFLP marker sequence). The hereby identified polymorphism is then detected using a molecular detection assay. For example, an AFLP marker may be sequenced and converted into a CAPS marker (cleaved amplified polymorphic sequence), detectable in a CAPS assay, the techniques of which are well known in the art (See Akopyanz et al., Nucleic Acid Research, 20:6221-6225 (1992) and Konieczny & Ausubel, The Plant Journal, 4:403-410 (1993)) or into an indel (insertion/deletion) marker. A CAPS assay involves amplifying the marker locus by PCR followed by digestion with restriction enzymes. An AFLP marker can also be converted into an STS marker or a SNP marker/assay using methods known in the art, or into any other derived molecular marker. Whenever referring to AFLP markers herein, it is understood that markers derived therefrom are encompassed as an embodiment, even if derived markers are not explicitly mentioned.

In one form of the invention, a cucumber plant is provided where—owing to the heterozygous presence of the compact gene—the progeny obtained by self-pollination has a segregated population with a ratio of about 1:2:1 between plants of the usual long cucumber lacking the compact gene, plants of the heterozygous (intermediate compact) type, and the compactly growing plants that are homozygous for the compact gene, or a population that splits into approximately 50% of plants of the usual type of cucumber lacking the compact gene and approximately 50% of compactly growing plants that are homozygous for the compact gene, after the doubled haploid production of the plant that is heterozygous for the compact gene. The invention also covers the above plants in which the phenotypical characteristics of the compact gene have a monogenic intermediate heredity and are mostly expressed in the phenotype (i.e. with the strongest compact phenotype) when the compact gene is in the homozygous state.

As mentioned above, the invention also covers heterozygous (e.g., hybrid) cucumber plants (and/or which may be suspected to comprise the compact gene in heterozygous form), in which the presence of the compact gene can be demonstrated by crossing these plants with gherkin or short cucumber plants and analysing the resulting F1 plants (and/or F2 plants) with the aid of the AFLP method and by the use of at least one, or at least 2, 3, 4, 5 or 6, of the following AFLP markers E14/M61_M873.6, E19/M50_M280.2, E24/M49_M211.5, E17/M54_M 179.0, E16/M47_M426.1, E16/M47_M411.0 and/or E16/M47_M402.9, or markers derived from these, or other polymorphic AFLP markers, which flank the compact gene, especially the AFLP markers E14/M61_M873.6 and/or E19/M50_M280.2, or markers derived from them, where the segregating F2 population obtained from the self-pollinated F1 plants in which the compact gene has been demonstrated exhibits co-segregation of the compact characteristics with at least one (or at least 2, 3, 4, 5 or 6, or all 7) of these AFLP markers or markers derived from them. Thus, the F1 plants obtained from a cross between a compact heterozygous and a gherkin or short cucumber will segregate 1:1 for the heterozygous compact characteristics:normal characteristics and the markers will co-segregate with the compact characteristics. The F2 families obtained by selfing the heterozygous compact F1 plants will segregate 1:2:1 for the homozygous compact:heterozygous compact:normal characteristics and the markers will co-segregate with the compact characteristics.

A marker which "flanks" the compact gene locus ("flanking marker") refers to a marker located on either side of the compact gene locus, i.e. a marker being on one side of the locus or on the other side of the locus. Preferably a pair of flanking markers is used in any of the marker assisted selection or detection methods described herein, with one flanking marker on one side and the other on the other side of the locus. However, a single flanking marker can also be used. In FIG. 1, for example, E14/M61-M873.6 and E19/M50-M280.2 is a pair of flanking markers, located at a distance of 0.05 cM and 0.67 cM, respectively.

The embodiments referring herein to specific AFLP markers linked to the compact gene are also applicable to other AFLP markers which are polymorphic between plants comprising the compact gene and plants lacking the compact gene and which are linked to the compact locus, as well as markers derived from these. Such other polymorphic AFLP markers can, for example, be found by making different segregating populations, and/or by screening more AFLP primer combinations, identifying polymorphic markers and mapping the markers near the compact locus. AFLP markers linked to the compact locus and which are polymorphic between long cucumber and plants comprising the compact locus can, thus, be found, and used according to the invention, for example to transfer the compact gene into another plant or to detect the compact gene in plants. This is only possible by using the compact plants according to the invention and was, therefore, not possible based on the prior art material.

In one form of the invention, the resulting plants of the usual type of cucumber with which the plants according to the invention are compared include about 25% of plants without compact growth, in a 1:2:1 segregating population generated by the self-fertilization of a plant that is heterozygous for the compact gene; or about 50% of plants without compact growth after the doubled haploid production of a plant that is heterozygous for the compact gene. In one of the embodiments of the invention, the plants of the usual cucumber type belong to the Sabrina or the Korinda variety. Thus, a plant suspected to be heterozygous for the compact gene can be analyzed/identified/selected by either a) selfing said plant and analyzing the selfed plants for a 1:2:1 segregation ratio of the homozygous compact:heterozygous compact:normal characteristics as described above or b) by producing double haploids (DH) from the plant and analyzing the 1:1 segregation of normal:homozygous compact characteristics in the DH plants.

The invention also covers cucumber plants homozygous for the compact gene and displaying compact characteristics. Such plants are suitable for introducing the compact gene into any other cucumber plant by crossing and selection and for detecting the presence of the compact gene in a plant. In one embodiment plants homozygous for the compact gene are plants of, or derived from, the long cucumber type seeds deposited under NCIMB 41266 (which are homozygous for the compact gene). Plants homozygous for the compact gene are preferably of the long cucumber type, but may also be other cucumbers types (short or gherkins, etc.).

The present invention also covers any of the above plants, comprising the compact gene, which can be derived from the seeds deposited with NCIMB Ltd. under number 41266 (seeds of long cucumber type plants which are homozygous for the compact gene) according to the Budapest Treaty by the company Nunza B.V. (now called Nunhems B.V.) on 29 Mar. 2005, the address of NCIMB Ltd. being Ferguson Building, Craibstone Estate, Bucksburn, Aberdeen AB21 9YA, Scotland. This is not restricted to plants with the entire set of the phenotypical and genotypic characteristics of the plants that are grown from these deposited seeds. The present invention also covers the seeds, cells or tissues of one of the above plants that comprise the compact gene in their genome, as well as plants grown from the above seeds and from the seeds, cells or tissues of these plants that possess the compact characteristics and are either heterozygous or homozygous for the compact gene according to the invention.

The present invention also covers cucumber plants and plant parts deposited under NCIMB number 41266 and cucumber plants and plant parts derived therefrom and comprising the compact gene in homozygous or heterozygous form. Thus, the compact gene is obtainable from the seed deposit and can be transferred to other cucumber plants by crossing a plant of said deposit (or a plant obtained by crossing and/or selfing a plant of said deposit) with another cucumber plant and obtaining progeny from said cross. Plants comprising the compact gene are thus obtainable from the deposited seeds via conventional breeding and any plants described herein are preferable obtained via conventional breeding and not via plant transformation (i.e. the plants are not transgenic plants). The cucumber plants comprising the compact gene and being derived/derivable from NCIMB 41266 are either long cucumbers, short cucumbers, gherkins, or others and are preferably indeterminate in their growth.

In one form of the invention, the compact gene is the gene that is flanked by the AFLP markers E14/M61_M873.6 and/or E19/M50_M280.2 in the case of hybridization between plants grown from seeds deposited under NCIMB number 41266 on the one hand, and short cucumber or gherkin plants on the other hand, especially in the case of hybridization with plants of a short cucumber line or variety, such as for example Manar F1.

The present invention also covers a method for crossing any of the above plants comprising the compact gene in homozygous or heterozygous form with other cucumber plants in order to introduce the compact gene into other plants of the species *Cucumis sativus*. In one embodiment plants, into which the compact gene has been transferred, are selected phenotypically based on one or more compact gene characteristics. The progeny may be direct progeny of the cross (F1) or progeny obtained by further selfing and/or crossing. In another embodiment of the invention the transfer may be additionally or solely be carried out, and/or wherein progeny are checked for the presence of the compact gene, with the aid of a technical process in which at least one polymorphic AFLP marker, or a marker derived therefrom, is used that flanks the compact gene, in the case of hybridization with a short cucumber or gherkin plant, or where a microbiological process of preparing doubled haploids or an in vitro cell culture is used.

Thus, a method for introducing the compact gene into a plant of the species *Cucumis sativus*, and/or for generating hybrid seeds of the species *Cucumis sativus*, is provided comprising the steps of:
(a) providing a *Cucumis sativus* plant lacking the compact gene, e.g. a normal long cucumber line or variety;
(b) crossing the plant of (a) with a *Cucumis sativus* plant comprising the compact gene, e.g. in homozygous form,
(c) obtaining the hybrid seeds from said cross.

Optionally, phenotypic analysis of the compact gene characteristics can be carried out in steps (a), (b) and/or (c). Optionally also, AFLP marker analysis may be carried out, by doing test crosses with short cucumber or gherkin and analyzing the presence/absence of the markers in progeny of those crosses.

Also, a method for determining whether a plant comprises the compact gene in homozygous or heterozygous form is provided, comprising the steps of:
(a) crossing the plant suspected to comprise the compact gene with a short cucumber plant or gherkin plant (lacking the compact gene) to obtain F1 plants, or selfing a plant suspected to comprise the compact gene to obtain S1 plants;
(b) analyzing the F1 or S1 progeny obtained from (a) with one or more AFLP markers or markers derived therefrom,
(c) selfing the F1 or S1 progeny comprising the compact gene obtained from (a) to obtain F2 or S2 plants and analyzing the F2 or S2 plants obtained with one or more AFLP markers or markers derived therefrom, and
(d) based on the co-segregation of AFLP markers and compact characteristics in step (b) and/or (c), concluding whether the original plant comprised the compact gene in homozygous or heterozygous form.

In another embodiment of this invention, an alternative method is provided, which is identical to the above method, but wherein step b) is omitted.

The AFLP markers used are those described elsewhere herein, i.e. the markers linked to the compact gene.

The above method implies that the plant phenotypes are also analyzed in steps b and c, i.e. that the presence or absence of compact characteristics is determined.

If the original plant is heterozygous for the compact gene, the F1 will segregate 1:1 for plants comprising AFLP markers linked to the compact gene (and having heterozygous compact characteristics) and plants lacking the AFLP markers (and lacking compact characteristics). The F2 obtained by selfing a plant comprising the compact gene will then segregate 1:2:1, for plants comprising the compact gene in homozygous form (and comprising the AFLP markers and compact characteristics):plants comprising the compact gene in heterozygous form (and comprising the AFLP markers and compact characteristics (in intermediate form)):plants lacking the AFLP markers and the compact characteristics. Likewise, if the original plant is heterozygous for the compact gene, the S1 will segregate 1:2:1 (1 homozygous compact:2 heterozygous compact:1 not compact/normal).

If the original plant is homozygous for the compact gene, all F1 plants will be heterozygous, comprising the AFLP markers and the compact characteristics, and the F2 will segregate 1:2:1 as described above. If the original plant is homozygous for the compact gene, all Si plants will be homozygous as well.

The present invention also covers a method for producing seeds of a hybrid cucumber plant by using one of the above plants comprising the compact gene in the homozygous state, in which hybrid the compact gene is present in the heterozygous state, and especially a method that involves the use of an in vitro cell culture, also covering the plants, the fruits and seeds of hybrid plants according to the invention that comprise the compact gene.

In one embodiment a method is provided for introducing the compact gene into a plant of the species *Cucumis sativus*, and/or for generating hybrid seeds of the species *Cucumis sativus*, such method comprising the steps of:
(a) providing a *Cucumis sativus* plant lacking the compact gene, e.g. a normal long cucumber line or variety;
(b) crossing the plant of (a) with a *Cucumis sativus* plant comprising the compact gene in homozygous form,
(c) obtaining the F1 seeds from said cross,
(d) generating doubled haploid (DH) plants from said F1 seeds or F1 plants using in vitro cell culture,
(e) selecting the doubled haploid plants which are homozygous for the compact gene and discarding the DH plants which lack the compact gene
(f) using the DH plants as a parent in a cross with a plant lacking the compact gene to produce a hybrid comprising the compact gene in heterozygous form.

In a further embodiment of the invention in vitro techniques are used to maintain and/or multiply plants according to the invention comprising the compact gene in homozygous or heterozygous form, for example to avoid multiplication via seeds and/or to multiply identical hybrids via in vitro techniques. Such methods involve, for example, clonal or vegetative propagation of plants according to the invention, using e.g. cell or tissue culture techniques. Thus, in vitro cell or tissue cultures of explants of plants comprising the compact gene are encompassed herein, as are a plurality of clonal or vegetative reproduced plants, comprising the compact gene, as well as seeds, fruits, flowers and tissues of those plants. In vitro techniques are known in the art, see e.g. Mohammadi and Sivritepe (2007, J of Biol. Sciences 7: 653-657), Ahmad and Anis (2005, Turk J Botany 29: 237-240) or Handley and Chambliss (1979, HortScience 14:22-23).

The invention also covers a method in which at least one (or at least 2, 3, 4, 5, 6 or all 7) of the AFLP markers E14/M61_M873.6, E19/M50_M280.2, E24/M49_M211.5, E17/M54_M 179.0, E16/M47_M426.1, E16/M47_M411.0 and/or E16/M47_M402.9, and especially the AFLP markers E19/M50_M280.2 and/or E14/M61_M873.6, or markers derived from them, are used to detect the presence of the compact gene in plants, fruits, seeds, plant tissues or cells in various stages of the plant breeding process, as well as covering such a method for the detection of the presence of the compact gene in biological material (e.g. DNA) coming from plants, seeds, cells or tissues.

Furthermore, one of the forms of the invention relates to a method for harvesting cucumber fruits with the aid of a harvesting robot, in which form the cucumber fruits grow on plants that comprise the compact gene, as well as relating to a method for the cultivation of cucumber plants by the highwire process, where the cucumber plants in question are one of the above plants, and especially a method of this kind where there are at least 5%, 10%, 15% or 20% more stems per $m^2$ than in the usual cultivation of cucumbers.

DETAILED DESCRIPTION OF THE INVENTION

The invention relates to cucumber plants with a specific gene, called herein the "compact gene", which is expressed in the (heterozygous or homozygous) compact phenotype by the formation of plants with a slower growth rate and a leaf that is smaller and darker and stays green for longer than in the case of the phenotype of the customary cucumber plant lacking this gene, such as normal long cucumber types (e.g. cultivar Korinda), when grown under the same environmental conditions. The leaves of this 'compact type' are more brittle than those of the usual type, so they break off more easily at the ribs. However, the broken leaves stay green and healthy, unlike the damaged leaves of the usual type of plant, which grow yellow and shrivel up sooner. Furthermore, the leaves of the compact type are horizontal and do not droop as they do in the case of the usual cucumber type. The compact phenotype therefore permits a better ventilation through the plant, and its open structure makes the plants and fruits more visible and so easier to work with. Also the flowers are smaller, having shorter and narrower petals (see also FIG. 2). The plants have also shorter lateral shoots and shorter internode length than plants lacking the compact gene. The plants of the homozygous compact phenotype themselves are less suitable for the standard commercial cultivation of long cucumbers, because they grow more slowly, but they are very useful for other types of cultivation and for the creation of hybrid (heterozygous) long cucumber plants that exhibit the phenotypic characteristics of the compact gene (called "compact characteristics") in the intermediate form. In commercial cultivation, mainly hybrid plants (heterozygous for the compact gene) are used that are obtained by crossing two genetically different parent lines. If one uses a parent line in which the compact gene is present in the homozygous state and hybridizes/crosses this plant with another parent line in which the compact gene is absent (such as a normal long cucumber variety or line), one obtains heterozygous hybrid plants that exhibit the unique combination of "compact characteristics" in an intermediate expression (the "heterozygous or intermediate compact" phenotype), thus obtaining hybrid plants with e.g. larger fruits and faster growth than plants of the "homozygous compact" type, but with e.g. shorter internodes than plants of the usual type lacking the compact gene in its genome. See FIGS. 2a, 2b and 2c, where the middle of each of the figures represents the heterozygous intermediate plant. The use of the plants according to the invention can also give a higher yield of fruit. Owing to their special combination of characteristics, the heterozygous hybrid plants according to the invention have an optimum growth, which permits less labour-intensive cultivation by the usual (greenhouse) method, in addition to which the yield is high, and so is the quality of the cucumbers obtained.

This optimum combination of characteristics, which is due to the expression of the compact gene according to the invention, is not known in the case of the usual long cucumber type. Previous hybrids formed with 'short cucumber' plant types and with gherkins have not led yet to this unique plant type (see also Table 2 in the Examples). It is difficult to transfer a desired characteristic from one plant to another by hybridization in plant breeding without transferring some other, undesirable characteristics, which are coupled to the desired ones. It is often impossible or particularly difficult to eliminate these undesirable characteristics by back-crossing and selection. The invention described here is unique in that it has been developed in the plants without any coupled negative characteristics, and with a simple genetical basis.

The compact gene according to the invention can also be introduced into other plants or can be combined with other useful characteristics produced by one gene or a few genes. For example, it is possible to create hybrids between plants comprising the compact gene and other cucumber plants by crossing plants with the plants according to the invention and cucumber plants comprising e.g. resistance to mildew (*Sphaerotheca fuliginea* (Schlecht. ex Fr.) and/or *Erysiphe cichoracearum* (DC. ex Mérat emend. Salm), also called the white disease), in order to produce resistant hybrids with the compact characteristics according to the invention, having either a full resistance or a partial (intermediate) resistance to disease. For example, the compact gene can also be introduced into cucumber plants having full mildew resistance, without necrosis occurring during winter cultivation, as described in published European Patent Application EP 1,433,378. It is also possible to obtain heterozygous compact hybrid plants with resistance to the cucumber vein yellowing virus (CVYV) (such as the resistance present in the reference variety Tornac), and/or with resistance to the cucumber yellow stunting disorder virus (CYSDV), see e.g. EP 1,317,558 or the PCT publication WO 2007/05,301. Furthermore, it is possible to obtain heterozygous compact hybrid plants with tolerance or resistance to *Didymella bryoniae* (black blotch or Mycosphaerella—van Steekelenburg, 1986), or with one or more pathogen-resistances, by using known cucumber species, as mentioned in the CPVO Protocol under Points 44-51 in Annex 1 (see the Literature).

The following definitions are included here to explain the invention and to help with the interpretation of the Claims and the description, but they are not intended to limit the scope of legal protection based on this Application.

"Molecular markers" are DNA based markers linked to a gene, allele or locus in the genome, which are detected using molecular methods and where the presence of the marker is indicative of the presence of the gene, allele or locus, such as markers based on nucleic acid hybridization (e.g. RFLP markers) or on PCR amplification (such as RAPD markers, AFLP markers, Single nucleotide polymorphism or SNP markers, or sequence tagged site or STS markers) or combinations of PCR and restriction enzyme analysis (such as CAPS markers), "AFLP markers" or Amplified Fragment Length Polymorphism markers are molecular markers well known in the art, which can be detected using AFLP analysis, making use of restriction enzymes and primer pairs which comprise a sequence complementary to the adapters used, an enzyme specific sequence, plus one, two or three selective nucleotides, as described by Vos et al. (1995). See also the Examples. Amplification results, for example, in a DNA band of a certain size on a polyacrylamide gel when amplifying template DNA comprising the marker (DNA region linked to the gene), while no band of that size may be present when using template DNA of a plant where the marker sequence is different (in which case the marker may herein be said to be "absent"). The size of the polymorphic band (marker) is indicated in the name of the marker, as are the restriction enzymes and primers used.

The term "comprising" is to be interpreted as specifying the presence of the stated parts, steps or components, but does not exclude the presence of one or more additional parts, steps or components.

"Phenotype" is the observable appearance of the plant resulting from the interaction between the genotype of the plant and its environment. It includes all the observable morphological and physiological characteristics of the plant.

"Genotype" is the totality of hereditary genetical information of an organism, which comes to expression in the phenotype in a particular way, partly under the influence of environmental factors.

"Cucumber plant" as used here denotes a plant, seed or embryo or any other plant part of the *Cucumis sativus* L.

species. The term "cucumber fruit" is used to refer specifically to the fruit. This cucumber fruit can be a gherkin, a long-, a short-, a mini-cucumber (Beith Alpha cucumber) or a midi-cucumber. The present invention also covers the cucumber fruits harvested from the plants according to the invention, as well as covering any use and any processing thereof A cucumber plant may be a cultivated plant or a breeding line, but is preferably not a wild plant or wild accession or Plant Introduction (PI)/genebank accession.

The "usual cucumber plant" of "usual cucumber plant type" or "normal" cucumber type is a cucumber plant as defined above, but lacking the compact gene according to the invention in its genome and lacking the compact characteristics (see further below). The compact gene can be introduced into such a usual plant by crossing and selection (phenotypic and/or marker based selection). Examples of the usual cucumber plant are long cucumber types, such as cultivars Korinda or Sabrina and others. Seeds that grow into the type plant Korinda (F1 hybrid) have been deposited by the applicant Nunhems B.V. at the NCIMB (Ferguson Building, Craibstone Estate, Bucksburn, Aberdeen, AB21 9YA, Scotland) under the Budapest Treaty under accession number NCIMB 41585 on 23 Sep. 2008. Korinda is a publicly available cucumber plant type well known to the cucumber breeder, but solely out of an abundance of caution, Applicant has deposited seeds for Korinda.

A plant "lacking the compact gene" or "without the compact gene" is herein referred to as a plant which does not comprise the (mutant) allele of the compact gene according to the invention (as for example obtainable from plants derived from seeds of NCIMB 41266) in its genome, which when otherwise present in the genome in one or two copies results in the (homozygous or heterozygous) 'compact characteristics' of the plant (as defined below). Instead, such a plant "lacking the compact gene" comprises (two copies of) the "wild type" allele of the compact gene, resulting in a "normal" phenotype, such as for example in cultivar Korinda. The "wild type" allele is, thus, the allele of the gene as found in normal cucumber plants and which results in the normal cucumber phenotype (not compact) when present in homozygous form.

The terms "cultivar" (abbreviated as "cv") and "variety" are used synonymously herein.

"Line" or "breeding line" is a group of plants with a very similar genotype and phenotype. It can be formed by the descendants of a plant after some generations obtained by self-fertilization or by vegetative multiplication using plant cells, cell cultures or tissue cultures, or by producing DH lines from a cucumber plant.

"Phenotypic selection" refers to the selection of plants based on one or more phenotypic characteristics, such as morphological and/or physiological characteristics, for example one or more compact characteristics can be selected phenotypically.

"Molecular marker based selection" refers to the selection of plants based on one or more molecular markers. For example, transfer of the compact gene from one plant to another can be done with the aid of one or more molecular markers linked to the gene, and/or presence or absence of the compact gene in a plant can be determined with the aid of one or more molecular markers linked to the gene.

"Hybridizing" or "hybridization" refers herein to crossing plants (cross pollinating one plant with another and obtaining progeny from the pollinated plant); in the context of nucleic acids, molecular binding of one nucleic acid to a complementary nucleic acid is referred to.

"Transformed plant" is a plant into which a chimerical homologous or heterologous gene is introduced via transformation as known in the art. In contrast, non-transformed plants do not comprise chimerical genes in their genome. The cucumber plants according to the invention are preferably non-transformed plants, obtainable by conventional breeding, into which the compact gene has been introduced without transformation methods and wherein the plant does not comprise all or parts of vectors or chimerical genes.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes. The plants of the compact type, i.e. the plants that comprise the compact gene according to the invention and which can be derived from the reference seeds deposited under NCIMB number 41266, include many different cucumber plants, with very different phenotypical characteristics and genotypical composition in comparison with those of the seeds deposited, but such a group of phenotypically different plants with only one shared characteristic (the compact gene) does not come under the above definition of a plant variety. Thus, the technical feasibility of making cucumber plants which comprise the compact characteristics is not limited to a single cucumber variety, but can be applied to any cucumber variety.

The phenotypic characteristics of the plants according to the invention and which are due to the presence of of the compact gene are called here "compact characteristics", and the plants that contain these characteristics are therefore called "compact plants", "compact types" or "compact plant types". These plants can be homozygous or heterozygous for the compact gene and are called respectively "homozygous compact" plants, compact types or compact plant type, and "heterozygous compact" or "intermediate compact" plants, compact types or compact plant types.

A monogenic "recessive" gene only has two phenotypic expressions, the dominant phenotype (whereby the plants homozygous and heterozygous for the gene all have the same dominant phenotype) and the recessive phenotype (whereby the plants homozygous for the recessive allele express the recessive phenotype). In contrast, a monogenic "intermediate" gene has three phenotypic expressions, whereby the homozygous recessive plants have a strong expression of the phenotypic characteristics, the homozygous dominant plants have a weak expression of the phenotypic characteristics and the heterozygous plants have phenotypic characteristics which lie between the strong and weak values. For the avoidance of doubt, the expression "lie in between" does not mean that the (mean) scores lie in the middle of the extremes, but means that the (mean) scores lie below the higher score and above the lower score.

"Intermediate expression" or "intermediate phenotype/ phenotypic expression" of the compact characteristics refers to the compact characteristics which plants comprising the compact gene in heterozygous form express, which lie in between the compact characteristics displayed by plants homozygous for the compact gene and plants lacking the compact gene. For example, internode length of compact heterozygotes is shorter than in plants lacking the compact gene but longer than in compact homozygotes. See also Table 1.

"Locus" is the place on the genome where a given gene is located.

"F1, F2, etc." refer to the succession of related generations obtained after crossing two parent plants or parent lines. The plants grown from seed that is obtained after crossing two parent plants are called 'F1' plants or hybrids. Self-fertilization of these F1 plants gives rise to an F2 generation, etc.

"Doubled haploids" (or DHs) are plants obtained by using a technical (in vitro) process for doubling the genome of haploid cells (such as pollen, microspore cells or egg cells) of a plant, and regenerating diploid plants from them, as is known from the prior art (e.g. from U.S. Pat. No. 5,492,827 or from the publication of Gémes-Juhász et al., 2002).

The term "hybrids", "F1 hybrids" or "hybrid plants" are used to denote the seed and the plants grown from that seed obtained by hybridizing two genetically different parent lines. F1 hybrid plants are characterized by the segregation of the typical characteristics in the following generation, i.e. in the F2 generation. These characteristics are therefore genetically unstable in the hybrids. Methods for developing hybrids are well known from the prior art (see for example the method described in U.S. Pat. No. 4,822,949). If one, for example, crosses a female parent line of the usual cucumber type lacking the compact gene with a male parent line comprising the compact type in homozygous form (or vice versa, if one crosses a female parent line comprising the compact gene in homozygous form with a male lacking the compact gene), one obtains F1 hybrids with an intermediate expression of the compact characteristics, which are of great interest in the commercial cultivation of cucumbers, such as the long cucumber, more especially in the case of high-wire cultivation.

"Short cucumber varieties or lines" or "short cucumber plants or types", as used here, are characterized by green fruits without, or practically without, the typical 'neck' (see the explanation in Point 23 in Annex 1 to the CPVO Protocol in the Literature), having a length of about 15-20 cm, with a smooth or slightly ribbed skin of the fruit and with parthenocarpic fruit formation. The leaves are generally medium large or large. Examples of the types of short cucumber varieties are the varieties Alamir and Turbulence, or cucumber plants that are awarded a score of 1-6 for the length of the fruit according to the CPVO Protocol (see Point 19 in Annex 1 to this protocol). Other examples of short cucumber varieties are: Manar, Beit Alpha, Maximum, Saric, Tornac, Kian, Arabella, Melita, Isatis, Vitara.

"Gherkin varieties or lines" or "gherkin plants", as used here, are characterized by medium green fruits, sometimes with a slightly lighter marbled tip, which have a length of about 12-15 cm, and a prickly skin with warts but often without ribs. The leaves are generally small or medium large. Examples of gherkin types are the Capra and Delphina varieties.

"Long cucumber varieties or lines" or "long cucumber plants" or "long cucumber type(s)", as used herein, are characterized by fruits of about 30-37 cm in length (or longer, for example 40 cm, 42 cm or more) with some neck and a lightly ribbed skin that is medium green in colour, and with parthenocarpic fruit formation. The leaves are generally large or very large. Examples of long cucumber types are the Sabrina and Korinda varieties, or cucumber plants that are awarded a score of 7-9 for the length of the fruit according to the CPVO Protocol (see Point 19 in Annexe 1 to this protocol). Other long cucumber varieties are, for example, Bodega, Bologna, Kamaro, Flamingo, Discover, Kalunga, Kasja, Logica, Millagon. Nicola, Milika, Manuela, Frida, Activa, Alaya, Savanna, Sienna, Bella, Sheila, Bornand.

In one embodiment of the invention the compact gene is present in long cucumber plants, short cucumber plants or gherkins, especially in indeterminate cucumber plants. "Indeterminate" cucumbers are cucumbers wherein plant growth is not terminated due to the sympodial bud being converted into floral tissue, i.e. the plants continue growing in length throughout the entire life cycle and also continue producing fruit throughout (i.e. in contrast to determinate cucumber plants, they do not come to fruit all at once). In a particular embodiment of the invention the compact gene is present in long-cucumber plants, especially in long-cucumber plants suitable for commercial cultivation, particularly in greenhouses. In one form of the invention this greenhouse cultivation is high-wire cultivation. In another form of the invention the compact gene according to the invention is present in cucumber plants that do not contain the Little Leaf locus (ll), present in the H-19 or Arkansas Little Leaf type, such cucumber plants being especially suitable for the commercial greenhouse cultivation of the long cucumber, more specifically by high-wire cultivation. In yet another embodiment of the invention the compact gene according to the invention is present in cucumber plants that do not contain the cp or cp-2 locus.

The "compact gene" is a genetic feature situated on a certain locus of the cucumber genome, which comes to expression in the phenotype of the compact plant by the formation of the typical compact characteristics defined herein, in comparison with, for example, the usual long cucumber type (such as plants of a customary long cucumber types, e.g. the Korinda variety).

The term "compact characteristics" used here denotes the totality of phenotypical characteristics of the features which are due to the presence in the plant genome of the compact gene according to the invention (in homozygous or heterozygous form). In one form of the invention several of these characteristics are inherited together with the compact gene to subsequent generations. The homozygous compact characteristics lead to even more compact plants with smaller petals and leaves and shorter fruits than the heterozygous compact gene. More specifically, the compact characteristics comprise a combination of the following (statistically significant) phenotypic characteristics (see also Table 1), which are conferred to a strong or intermediate degree when introduced into the normal long cucumber lacking the gene: a shorter stem length at 15 internodes, shorter internodes, smaller leaves, smaller flowers, and shorter fruits. In one form of the invention, the compact characteristics cover a combination of the following characteristics: a shorter stem length at 15 internodes, slower growth rate, shorter internodes, leaves that are smaller, more horizontal (erect), flatter (less bumpy or tuberculate), darker green, and more brittle (can be broken off more quickly), smaller flowers, smaller and lighter fruits, and especially the characteristics that are evident in plants that are homozygous for the compact gene (such as the homozygous plants grown from the seeds deposited under NCIMB number 41266, or doubled haploid plants that are homozygous for the compact gene and which are obtained from a plant that is heterozygous for the compact gene), which plants have significantly shorter stem length at 15 internodes, shorter lateral shoots, shorter internodes, smaller leaves, smaller flowers and shorter fruits—all this in comparison with plants of the wild type (i.e. without the compact gene), such as plants of the usual cucumber type, where we have e.g. about 25% of the plants without compact growth in a 1:2:1 segregating population after self-fertilization of a plant that is heterozygous for the compact gene, or about 50% of the plants without compact growth, obtained after doubled haploid production from a plant that is heterozygous for the compact gene. "About 25% of plants" and "about 50% of plants" is well understood by the skilled person having knowledge of genetics and heredity as referring to Mendelian segregation of a certain characteristic. In a population of 100 plants segregating for a certain characteristic in a 1:2:1 ratio, i.e. about 25% :about 50%:about 25% of plants having a normal:intermediate compact:compact phenotype, it is understood that it is not necessary that exactly 25, 50 and 25 plants have the described phenotypes, as genetic and non-genetic factors can influence the Mendelian segregation, but that statistically about 25%, 50% and 25% are of the mentioned phenotypes.

The above compact gene characteristics are, thus, a number of phenotypic characteristics which are inherited with the compact gene and are thus introduced into a plant into which the compact gene is introduced. The strength of the characteristics depends on whether the compact gene is present in homozygous or heterozygous form. The compact characteristics are thus either compared between the normal cucumber (lacking the compact gene) and a cucumber comprising the compact gene in homozygous or in heterozygous form, or between a plant comprising the compact gene in homozygous form and a plant comprising the compact gene in heterozygous form. It is understood that the comparison of such characteristics always involves the comparison of mean values of a number of plants grown under the same conditions (e.g. at least 10, 15, 20 or more plants) in order to account for any plant-to-plant variation.

The plants that are homozygous for the compact gene according to the invention are identified the most easily by their pronounced compact characteristics that are significantly different from those of the plants of the wild type (those without the compact gene, e.g. the Korinda variety), especially as regards the stem length at 15 internodes (significantly shorter than the wild type in homozygous form), the length and width of the leaves (significantly smaller than in the wild type in the homozygous state), the area of the leaf blade (significantly smaller than in the wild type in the homozygous state), the length and width of the petals (significantly smaller than in the wild type in the homozygous state), the weight of the fruits (significantly smaller than in the wild type in the homozygous state), the length of the fruits (significantly shorter than in the wild type in the homozygous state) and the number of internodes on the lateral shoots (significantly fewer than in the wild type in the homozygous state). FIGS. 2A, 2B and 2C attached show the clearly recognizable phenotypical differences between the normal long cucumber (as exemplified by the Korinda variety), and the heterozygous and homozygous compact plants according to the invention as regards the length of the fruits, the size of the leaves and the size of the flowers.

In one form of the invention a plant that is homozygous for the compact gene according to the invention is characterized by a combination of the following typical compact characteristics, as compared—under the same growing conditions (with sowing preferably in the summer, i.e. under Dutch summer greenhouse conditions, but possibly throughout the year)—with a plant that does not have the compact gene (called here the control plant, such as cucumber varieties or lines of the same type lacking the gene), on the basis of the mean values of measurements on at least 20 plants of each type, i.e. homozygous compact plants on the one hand and the control plants, on the other hand:

- the maximum width of the tenth true leaf 39 or 35 days after sowing the plants with the compact gene in the homozygous state is at most 70%, preferably at most 60% of the width of the tenth leaf on the control plants 39 or 35 days after sowing;
- the area of the leaf blade (0.5 times the maximum width of the leaf times the greatest length of the leaf from the lowest leaf lobe point to the tip of the leaf) on the tenth true leaf 39 or 35 days after sowing the plants with the compact gene in the homozygous state is at most 50%, preferably at most 40%, of the leaf blade area on the control plants 39 or 35 days after sowing
- the maximum width of the petals 39 or 45 days after sowing the plants with the compact gene in the homozygous state is at most 75%, preferably at most 70%, of the maximum width of the petals on the control plants 39 or 45 days after sowing
- the length of the lateral shoots 56 days after sowing the plants with the compact gene in the homozygous state is at most 60%, preferably at most 50%, of the length of the lateral shoots 56 days after sowing the control plants (the length is taken from the point where the lateral shoot is attached to the main stem to the end of the lateral shoot) and
- the number of internodes on the lateral shoots 56 days after sowing the plants with the compact gene in the homozygous state is at most 70%, preferably at most 60%, of the number of internodes on the lateral shoots 56 days after sowing the control plants.

A control plant used in the above comparative test can be e.g. a derived plant that does not contain the compact gene and is, for example, selected from a segregating population after self-pollination of a plant that is heterozygous for the compact gene, or it can be a plant from the approximately 50% of doubled haploid (DH) population coming from a plant that is heterozygous for the compact gene (without the compact gene), or else a cucumber plant that is representative of the same type of cucumber plant without the compact gene, e.g. a plant of the long cucumber type, such as a plant of the Korinda or Sabrina varieties of cucumber.

Thus, plants with the compact gene can be always identified on the basis of the unique combination of the above obvious phenotypical characteristics in plants that are homozygous for the compact gene. Making the plant homozygous for the compact gene is a standard procedure in the prior art, just as it is standard practice to obtain plants that are heterozygous for the compact gene from a plant that is homozygous for this gene. These heterozygous compact plants are also the subject of the present invention.

The phenotypical characteristics of a plant, such as the size of the leaves, can show some differences according to the method of cultivation and the environmental factors (e.g. temperature, light, moisture and amount of nutrients), so it is obvious that preferably the same growing conditions are used, e.g. the standard/traditional method of cucumber cultivation or the high wire method may be used, for a comparison between the wild type (lacking the compact gene) and the heterozygous and/or homozygous plants according to the invention, all of which are grown under the same conditions.

The compact characteristics can be identified e.g. in hybrid plants, heterozygous for the compact gene, by comparing the characteristics of derived plants obtained after self-pollination or after the formation of a doubled haploid, starting with a plant suspected of containing the compact gene, and by establishing that the compact characteristics are passed on together according to the pattern expected from heterozygous, homozygous and wild plants (lacking the compact gene) in accordance with monogenic, intermediate inheritance. In the mutual hybridization (or self-pollination) of homozygous plants, there is no segregation of characteristics, but the inheritance of the compact characteristics can still be demonstrated here after the self-pollination of plants obtained by crossing a plant that is homozygous for the compact gene with (homozygous) plants of the wild type, such as the long cucumber plants known from the prior art, e.g. plants of the Korinda variety.

As used herein, the compact gene locus is the locus that—after introduction into the short cucumber or gherkin plants by hybridization—is flanked by at least one of the following AFLP markers E14/M61_M873.6, E19/M50_M280.2, E24/M49_M211.5, E17/M54_M 179.0, E16/M47_M426.1, E16/M47_M411.0 and/or E16/M47_M402.9, and especially by the AFLP marker E14/M61_M873.6 (at approximately 0.05 cM) and/or E19/M50_M280.2 (at approximately 0.67 cM), or markers derived from one of these AFLP markers (such as the STS or SNP markers or CAPS markers), more specifically in the hybridization of plants grown from the seeds deposited under NCIMB number 41266 with short cucumber or gherkin plants, e.g. short cucumber plants of the Manar F1 type.

What indicates the presence of the compact gene according to the invention in the heterozygous plant is the segregation of the compact characteristics in a ratio of 1:2:1 after the self-fertilization of a heterozygous cucumber plant, with about 25% of the homozygous compact type, about 50% of the heterozygous compact type and about 25% of the wild type (having no compact characteristics or compact gene), or in a ratio of 1:1 in the doubled haploids, where about 50% of the DHs are homozygous for the compact gene and the other approximately 50% are homozygous for the wild type (i.e. without the compact gene). This can be established by the AFLP marker analysis of hybrids formed with a short cucumber or a gherkin plant, as described below, if these compact characteristics co-segregate with the specified AFLP markers that flank the compact gene in a hybrid formed with the short cucumber or gherkin plant. In this phenotypical comparison of the segregating cucumber plants, the same growth conditions are of course used and the same comparative measurements and observations are made at the same points in time. If extra control plants are included, they can be chosen from amongst plants of the usual long cucumber type, such as plants of the Sabrina or Korinda variety, especially plants of the Korinda variety. Selfing of a plant lacking the compact gene will result in all progeny lacking the plurality of compact characteristics.

The AFLP markers according to the invention can be used to establish that the plants in question contain the compact gene according to the invention. This can be done on the basis of the co-segregation of the compact characteristics, with a certain locus on the cucumber genome (as determined by the AFLP markers according to the invention) after hybridization of the plant to be analyzed with a short cucumber or a gherkin plant and marker and/or phenotypic analysis in the F1 and/or F2 generation obtained. Marker analysis is not an essential step because of the clearly observable phenotypical compact characteristics, shown in FIG. 2 and indicated in Tables 1 and 2.

For the marker analysis, a possibly hybrid cucumber plant suspected of being heterozygous for the compact gene is crossed with a gherkin or a short cucumber plant. Most of the short cucumber and gherkin varieties or lines can be used for this purpose, provided that the AFLP markers can be employed in that background. For easy phenotyping, it is best to use short cucumber or gherkin plants from a homozygous line with a phenotype that is as different as possible from that of the compact plant according to the invention with which it is crossed (e.g. a large-leaved short cucumber type with light-coloured leaves). Particularly suitable are the short cucumber types that are identified at least by the AFLP marker E16/M47_M426.1, e.g. plants of the well-known short cucumber variety Manar F1, or homozygous plants with a phenotype similar to that of the Manar F1 variety.

In this hybridization between a possibly hybrid cucumber plant (which is heterozygous for the compact gene) and a gherkin or short cucumber plant, the compact characteristics are present in a ratio of 1:1, with about 50% of the plants having the compact characteristics (and the flanking AFLP markers), and the rest not. After the self-pollination of the plants with the compact characteristics obtained from this hybridization with a gherkin or a short cucumber plant, we obtain an F2 plant, which shows a segregation in a 1:2:1 ratio between plants that are homozygous for the compact gene or the compact characteristics (and comprise the flanking AFLP markers), plants that are heterozygous for the compact gene or the compact characteristics (and comprise the flanking AFLP markers), and plants of the wild type, which lack the compact gene or the compact characteristics, (and lack the flanking AFLP markers) provided that the original (hybrid) plant was indeed heterozygous for the compact gene.

Marker analysis with at least one of the AFLP markers E14/M61_M873.6, E19/M50_M280.2, E24/M49_M211.5, E17/M54_M179.0, E16/M47_M426.1, E16/M47_M411.0 and/or E16/M47_M402.9, and best of all with the marker E14/M61_M873.6 and/or E19/M50_M280.2, can then be carried out for genotyping these plants. When comparing the phenotypical analysis (the segregation of the phenotypical compact characteristics) with the genetic analysis (segregation of at least one of the markers in the short cucumber or gherkin hybridization), the aim is to establish the co-segregation of the compact characteristics according to the invention with the AFLP markers that occurs if the compact gene according to the invention is present in these plants.

In a form of the invention several of the phenotypical characteristics of the compact plants according to the invention (the compact characteristics) are inherited jointly by the descendants of the compact plants according to the invention. The co-segregation of one or more of the AFLP markers according to the invention (such as one of the AFLP markers shown in FIG. 1) with the compact phenotype indicates the presence of the compact gene in the plants according to the invention.

As a result of more plant breeding work, the compact gene is further introduced into other genetic backgrounds by hybridization. It is possible that the compact characteristics are less easy to detect phenotypically in plants and hybrids that are heterozygous for the compact gene. However, the compact gene can always be identified on the basis of the above-mentioned segregation of the compact characteristics after the self-fertilization of plants that are heterozygous for the compact gene, or after the formation of doubled haploids. This phenotypical analysis can be confirmed by the above marker analysis. The combination of several compact characteristics in plants that are homozygous for the compact gene can be established in a segregating population by anyone with ordinary competence who is involved in the cultivation of cucumbers. Plants that contain the compact gene can always be recognized in this way.

In a specific embodiment of the present invention, the compact gene is present in the homozygous state. Such plants are very useful as parent lines for the production of hybrid cucumber plants, comprising the compact gene in heterozygous state and having an intermediate phenotype.

In another specific embodiment of the present invention, the compact gene is present in the heterozygous state if one hybridizes a plant of the homozygous compact type with a plant without the compact gene (e.g. a plant of the usual long cucumber type). The hybridization of the homozygous compact type with other plants represents other specific embodiments of the invention that are different from the embodiment presented in the examples.

The present invention also covers the use of the compact gene in other cucumber varieties and lines or in other plants of the *Cucumis* genus by introducing this compact gene into other plants by hybridization using the well-known general methods (such as for example recurrent selection, embryo rescue, etc.), the recipient plants being e.g. other plants of the *Cucumis sativus* species, especially plants of the long cucumber type.

The present invention also covers the detection and monitoring of this compact characteristic in the various hybridization products and stages of the plant breeding process with the aid of at least one of the AFLP markers E14/M61_M873.6, E19/M50_M280.2, E24/M49_M211.5, E17/M54_M179.0, E16/M47_M426.1, E16/M47_M411.0 and/or E16/M47_M402.9, especially with the marker E14/M61_M873.6 and/or E19/M50_M280.2, or markers derived from these (such as the STS, SNP or other markers derived from at least one of these AFLP markers) after hybridization-based introduction into short cucumbers or gherkins, as described above. The present invention also covers kits containing such markers. The AFLP technique and the AFLP markers are described in detail in EP 0,534,858 B1, and the contents of that document and the definitions given there in Section 5.1 on pages 4-6 can also be used for the purposes of the present invention. In short, the use of AFLP markers comprises the following steps: a) providing genomic DNA of cucumber plants to be analyzed, b) restricting the genomic DNA of each plant with two restriction enzymes, such as herein EcoRI and MseI, c) ligating adapters to both ends of the restricted fragments, whereby the adapters are specific for the restriction enzymes used, i.e. EcoRI and MseI adapters, d) amplifying a subset of the restriction fragments by PCR, using the primer combinations described for the markers (for example the primer pair E14 and M61 to amplify a band of about 873 bases or the primer pair E19 and M50 to amplify a band of about 280 bases if the compact gene is present in the DNA of the plant). The AFLP primers comprise a part that is complementary to the adapter sequence (core sequence) and a part of the restriction enzyme recognition sequence, and further contain in addition 1, 2 or 3 selective nucleotides. E14 and E15 for example contain 2 selective nucleotides, while M61 and M50 contain 3 selective nucleotides. The AFLP primer and adapter sequences are known in the art.

The following examples are given to illustrate one of the embodiments of the invention without intending to restrict the scope of the protection, which is specified in the Claims attached.

BRIEF DESCRIPTION OF THE DRAWINGS

FIG. 2 shows a comparison of fruits, flowers and leaves of plants obtained under the same conditions of cultivation (always removed 35-40 days after sowing), the leaf being the 15th leaf in every case.

EXAMPLES

Example 1

Phenotype Analysis of the Compact Plants

Figure 1:
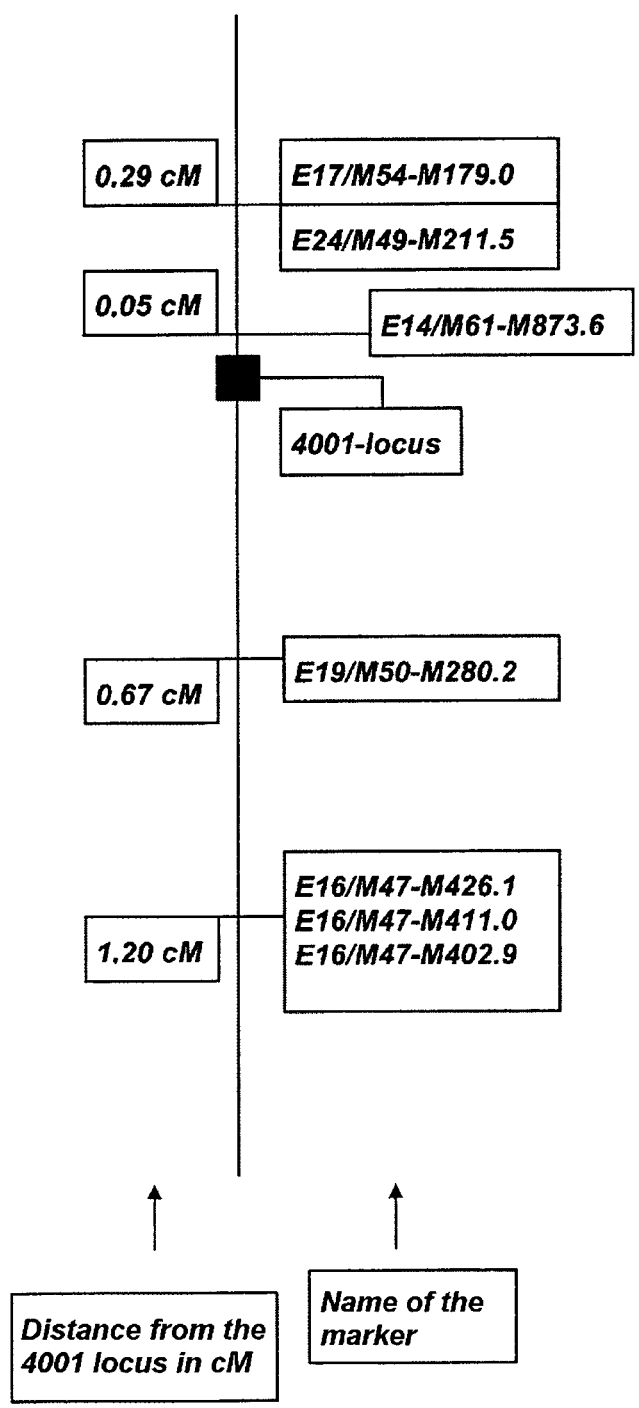
FIG. 1 shows a genetic map of the compact locus, referred herein to as "4001-locus" (see Example 2). The genetic map of the 4001 locus is shown, with EcoRI/MseI AFLP markers on it, which can be used to detect the presence of the compact gene in hybridization of plants with a short cucumber or gherkin plant. The genetic distances are based on the F2 population consisting of 4180 individuals resulting from the hybridization of a plant 4001 (homozygous for the compact gene) with Manar F1 (short cucumber).
Figure 2A:
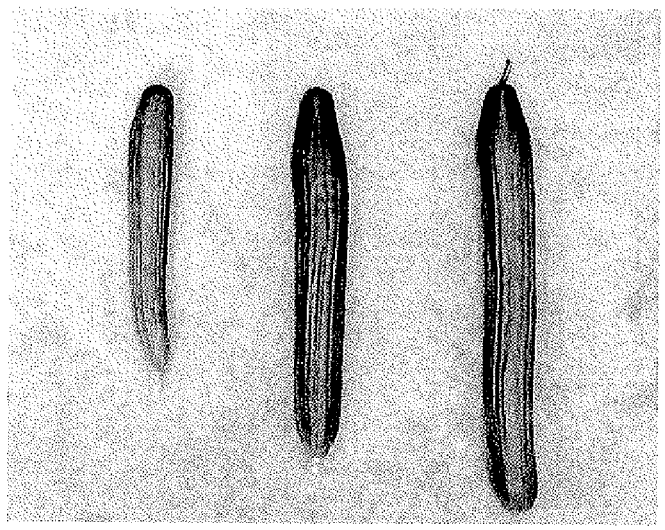
FIG. 2*a* shows a comparison of typical fruits harvested from plants that were homozygous for the compact gene (left), from plants that were heterozygous for the compact gene (middle) and from control plants of the Korinda type, lacking the compact gene (right).
Figure 2B:
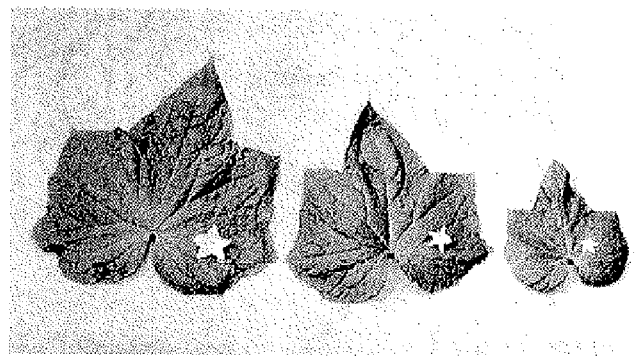
FIG. 2*b* shows a comparison of typical leaves and flowers removed from plants that were homozygous for the compact gene (right), from plants that were heterozygous for the compact gene (middle) and from control plants of the Korinda type (left).
Figure 2C:
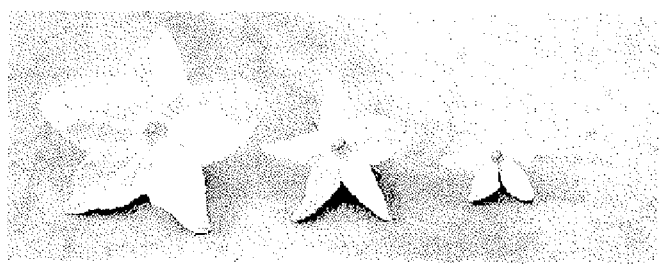
FIG. 2*c* shows a detailed comparison of the petals of typical flowers removed from plants that were homozygous for the compact gene (right), from plants that were heterozygous for the compact gene (middle) and from control plants of the Korinda variety (left).

A more compact plant with a deviant phenotype was unexpectedly found in an F1 hybrid population when cultivating the long Dutch cucumber in the Netherlands. This plant was called the "4001 type", and the locus responsible for it was called the "4001 locus". It was established that, in comparison with other long cucumber plants like those of the Korinda variety, for example, the growth of the compact plants was moderate, and its main stem grew slowly, mainly because its internodes were shorter. The leaves of this more compact plant were noticeably smaller and darker than those of the usual long cucumber variety. The foliage of the more compact plants was more horizontal, and the leaves were less bumpy, i.e. they were flatter. The more compact plants had a noticeably more open plant structure than the usual long cucumber variety. Its fruits were shorter and weighed less than on plants of the long cucumber type.

Analysis of a population of these plants, obtained by the self-fertilization of plants that were heterozygous for the 4001 locus (also called compact locus) showed that the compact characteristics segregated in the way expected from monogenic, intermediate heredity. Beside the heterozygous intermediate type, there were also plants that were homozygous for the typical compact characteristics described above, such as a very compact growth, small leaves, short fruits and short internodes.

The segregation pattern of the plants was found to be as follows:
  about 25% of them were homozygous compact plants
  about 50% of them were heterozygous intermediate compact plants
  about 25% of them were normal long cucumber plants.

This Mendelian segregation ratio of 1:2:1 points to the segregation of one gene on a single locus, with the intermediate phenotypic expression of the heterozygous genotype. Seeds of the homozygous plants of the 4001 type (*Cucumis sativus* ssp. *sativus*) were deposited on 29 Mar. 2005 by the company Nunza B.V. (whose name has since been changed to Nunhems B.V.) with NCIMB (address: Ferguson Building, Craibstone Estate, Bucksburn, Aberdeen, AB21 9YA, Scotland) under NCIMB number 41266 in accordance with the Budapest Treaty. Whenever applicable, the Applicant requests that samples of this biological material and any material derived therefrom be only released to a designated expert in accordance with Rule 32(1) EPC or related legislation of countries/regions or treaties having similar regulations, until the mention of the grant of the patent, or for 20 years from the date of filing if the application is refused, withdrawn or deemed to be withdrawn.

In haploid cells, e.g. pollen, microspore cells or egg cells of cucumber plants that are heterozygous for the compact gene, the compact gene should be either present or absent. Analysis of doubled haploids (abbreviated here as DH) obtained from plants that were heterozygous for the compact gene indeed gave the following result:

about 50% of the DHs exhibited the homozygous compact plant type due to the presence of the compact gene in the homozygous state and about 50% of the DHs exhibited the normal plant type, due to the absence of the gene for compact characteristics. These plants are homozygous for the normal long type of cucumber.

In the segregation ratio for doubled haploids, only the 2 different homozygous genotypes occur, in a 1:1 ratio. This indicates that it is definitely a single locus that is involved here, and most probably a monogenic characteristic.

To raise the agricultural value of other cucumber cultivars, hybrids were produced between homozygous compact plants and various cucumber plants of the long type. The long types that were used were long types suitable for spring, summer and autumn conditions and long types with various disease resistances (with intermediate resistance or resistance to powdery mildew (*Sphaerotheca fuliginea* and/or *Erisyphe cichoracearum*); with resistance to CVYV, CMV and/or CYSDV). These hybrids and their further selection led e.g. to plants that had a better resistance to disease and gave longer fruits than the homozygous compact plants, but which still contained the compact gene and had a more open plant form. The hybrids produced, thus, contained the intermediate compact phenotype and were suitable for traditional greenhouse cultivation or high-wire cultivation. Thus, all such derived plants in different genetic backgrounds had useful characteristics and displayed the favourable compact characteristics.

The above specific product in the homozygous state and the specific product in the heterozygous state were compared for a number of relevant characteristics with the usual long cucumber type, using the Korinda variety as an example, and the results are shown in Table 1.

Table 1 shows a comparison between the usual long cucumber type (normal type of the Korinda variety), the homozygous 'compact type' and the heterozygous intermediate type for features that are clearly characteristic of these types of plant. The seeds for these comparative trials that gave the results in question were sown on 4 Jul. 2005. The seedlings were transferred into rockwool pots on 8 Jul. 2005 in a nursery greenhouse belonging to the Nunhems Company in Nunhem, the Netherlands, where the normal practical conditions used by cucumber producers prevailed. On 26 Jul. 2005, the young cucumber plants were transferred into a production type cucumber greenhouse with rockwool mats and standard nutrients for cucumbers. The plant density was about 1.2 plants per $m^2$. The plants were made to grow up to the wire in the usual way. They were attached to it and "topped" there, after which the top 3 lateral shoots were retained and allowed to grow. The first 6 axils below on the main stem (without any fruit) were cleaned up, after which 2 fruits were kept (at the 7th/8th axil) and then some axils were again cleaned up, so that the bottom fruits could develop easily. The observations presented below were made on at least 20 plants of each type, and the resulting mean values of the measurements are listed in Table 1.

The dates on which the measurements listed in Table 1 were taken are also given in the table. Since these absolute values vary with the time and place of the measurements or observations, the percentages relative to the normal type are also given for the measured and calculated values obtained for the heterozygous and the compact type.

Explanation of the Terms Used in Table 1

CBP code: The numbering according to the CPVO Protocol (see the Literature)

Obser. type: (type of observation)
  M=Measurement in centimeters (cm), grams (g) or numbers
  C=Calculation, V=Visual observation % of N: The observed value for the heterozygous or the homozygous compact type, expressed as a percentage of the value obtained for the normal or wild type LSD: Least significant difference according to the Scheffe's paired test (1953, 1959) at a probability value of 0.5% and 0.1% or a reliability level of 95% or 99%, respectively.

Signif. diff.: NS=not significant
  *=significant at the 5% level
  **=highly significant at the 1% level
  N/H=between the normal and the heterozygous type
  N/C=between the normal and the homozygous compact type
  H/C=between the heterozygous and the homozygous compact type Description of the Characteristics Listed in Table 1

Plants

Growth rate: length of the stem 44 days after sowing, measured from the substrate Length of the stem with 15 internodes: length of the stem measured from the substrate over 15 internodes Length of the lateral shoot: length between the point where the main stem is attached and the tip of the lateral shoot 56 days after sowing Number of internodes on the lateral shoot: total number of internodes on the lateral shoot 56 or 66 days after sowing Leaves Leaf 1: the $10^{th}$ leaf (height about 1-1.5 m)

Leaf 2: the $11^{th}$ leaf (height about 1-1.5 m)

Length: greatest length of the leaf from the lowest leaf lobe point to the tip of the leaf (different from the leaf length used in the CPVO Protocol)

Width: maximum width of the leaf (see the CPVO Protocol in the Literature, and specifically the text in Point No. 11 under "Explanations and Methods" in Annexe 1)

Length/width ratio: the length of the leaf divided by its width

Area of the leaf blade: 0.5 times the leaf width times the leaf length, in $cm^2$ Orientation: 1 is hanging down vertically, 9 is horizontal Intensity of the green colour: 1 is light green, 9 is dark green Bumpiness: 1 is very bumpy, 9 is a flat leaf Brittleness: a measure of the ease of breaking the leaf off by hand; 1 is flexible, 9 is brittle Flowers Length of the petals: greatest length of the petals from the point of attachment to the tip Width of the petals: maximum width of the petals
Length/width ratio of the petals: length of the petals divided by their width
Fruits
Weight: mean weight of 2 fruits per plant in grams, divided by 2
Length: the length measured from the insertion of the fruit stalk in the fruit to the insertion of the flower in the fruit With the compact characteristics being so clear to see, Table 2 shows the data obtained by a comparison of the visual characteristics of the normal (long) cucumber type (using Korinda as an example), the short cucumber type, the gherkin and the (homozygous) compact type. Table 2 presents a survey of the differences and similarities between all these cucumber types. The last column gives the overlap between the homozygous compact type and the gherkin (C/G) and between the compact type and the short cucumber (C/Sh). Since there is no overlap in the case of many of these characteristics, we have here a clear illustration of the unique combination of the characteristics of the compact type. In the visual scale used for this purpose, 1 is the lowest or shortest form of expression, and 9 is the highest or longest form of expression, the abbreviations being the same as in Table 1.

In the initial measurements made on these plants, we also found a significant difference in the chlorophyll content of the leaves of the homozygous compact plants in comparison with the normal long cucumber (using Korinda as an example), which explains the darker green colour of the leaves of the plants with the compact gene.

Figure 3A:
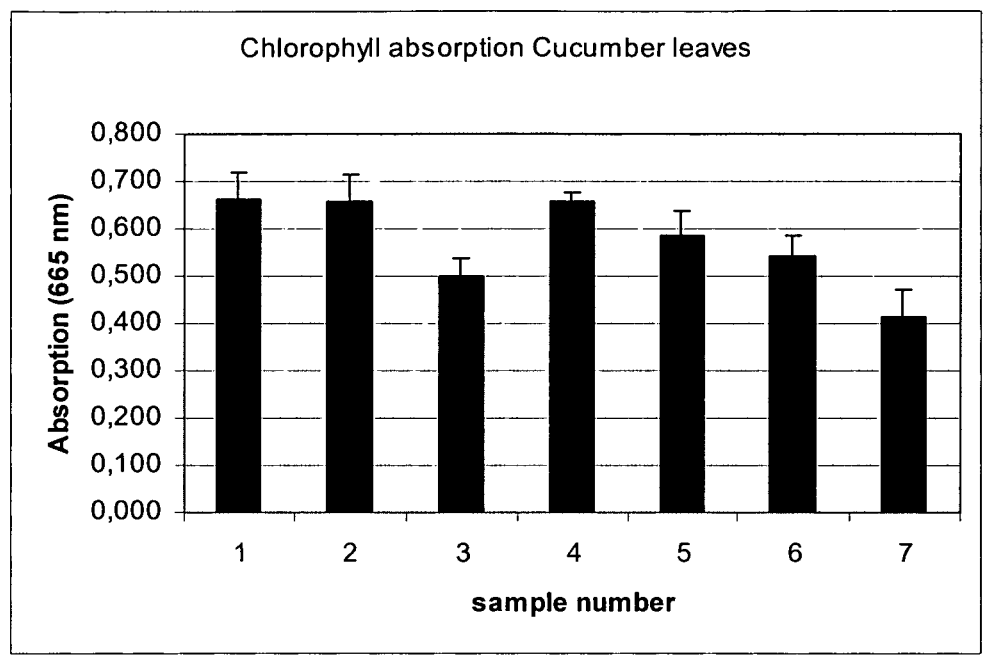
FIG. 3 shows chlorophyll absorption (FIG. 3*a*) and chlorophyll concentration ($\mu$g/g) (FIG. 3*b*) in leaf samples of plants homozygous for the compact gene (samples 1 and 4), plants heterozygous for the compact gene (samples 2, 5 and 6) and in normal cucumber plants (samples 3 and 7).
Figure 3B:
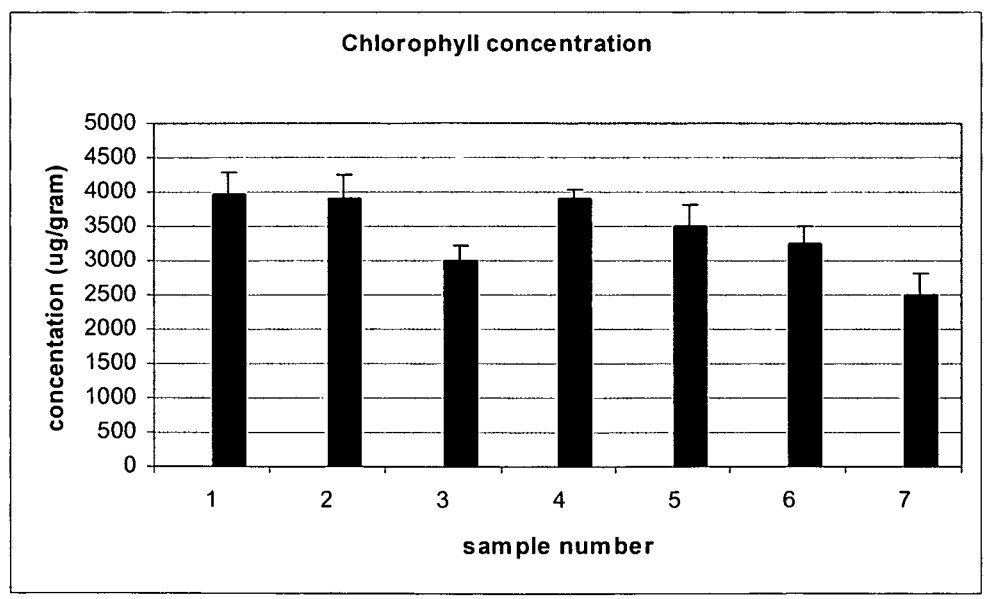

In order to determine chlorophyll content, three leaf discs (disc size number 6) were sampled randomly per leaf sample from homozygous compact plants (samples 1 and 4), heterozygous compact plants (samples 2, 5 and 6) and normal long cucumber plants (samples 3 and 7) grown under standard Dutch summer greenhouse conditions, at 65 days after sowing. The discs were placed into 5 ml ethanol and diluted 1×. Absorption at 665 nm was measured, the results of which are shown in FIG. 3a. Absorption was converted into chlorophyll concentration per gram leaf tissue using the following conversion:

Chlorophyll concentration (µg/ml)=25,13×A665×dilution factor
Chlorophyll concentration (µg per gram)=25,13×corrected A665×volume extract×dilution factor/mass.
Chlorophyll concentrations of the samples are shown in FIG. 3b.

The dark green color of leaves from plants comprising the compact gene correlates thus indeed with significantly higher chlorophyll content in homozygous compact and heterozygous compact (more than 3000 or 3500 µg/gram leaf) plants compared to plants lacking the compact gene (less than 3000 µg/gram leaf). Chlorophyll content of leaves can, thus, also be used as a compact characteristic to identify plants according to the invention and to differentiate such plants from normal plants lacking the compact gene.

Example 2

Characterization Based on DNA Markers

The location of the compact gene in the cucumber genome can also be demonstrated with the aid of molecular markers.

The compact gene was mapped by means of an AFLP analysis (see P. Vos et al., 1995).

The much-used restriction enzyme combination EcoRI/MseI was employed for the AFLP analysis. The letter E of EcoRI and the letter M of MseI are given in the name of the marker as is general practice in the literature. The code that comes after the letter E or M corresponds to the selective nucleotides on the 3' terminal site of the EcoRI and MseI primers, as is similarly standard practice (see the available list with AFLP codes on the websites www.keygene.com/keygene/pdf/KF%20Primer%20enzyme%20combinations.pdf and http://wheat.pw.usda.gov/ggpages/keygeneAFLPs.html).

For the restriction enzyme EcoRI (E), for examples, the selective nucleotides at the 3' end (−3) and the corresponding primer codes are as follows:

| | | | | |
|---|---|---|---|---|
| Primers + 0 | | E00 | | |
| Primers + 1 | A-3 | E01 | | |
| | C-3 | E02 | | |
| | G-3 | E03 | | |
| | T-3 | E04 | | |
| Primers + 2 | AA-3 | E11 | | |
| | AC-3 | E12 | | |
| | AG-3 | E13 | | |
| | AT-3 | E14 | | |
| | CA-3 | E15 | | |
| | CC-3 | E16 | | |
| | CG-3 | E17 | | |
| | CT-3 | E18 | | |
| | GA-3 | E19 | | |
| | GC-3 | E20 | | |
| | GG-3 | E21 | | |
| | GT-3 | E22 | | |
| | TA-3 | E23 | | |
| | TC-3 | E24 | | |
| | TG-3 | E25 | | |
| | TT-3 | E26 | | |
| Primers + 3 | AAA-3 | E31 | GAA-3 | E63 |
| | AAC-3 | E32 | GAC-3 | E64 |
| | AAG-3 | E33 | GAG-3 | E65 |
| | AAT-3 | E34 | GAT-3 | E66 |
| | ACA-3 | E35 | GCA-3 | E67 |
| | ACC-3 | E36 | GCC-3 | E68 |
| | ACG-3 | E37 | GCG-3 | E69 |
| | ACT-3 | E38 | GCT-3 | E70 |
| | AGA-3 | E39 | GGA-3 | E71 |
| | AGC-3 | E40 | GGC-3 | E72 |
| | AGG-3 | E41 | GGG-3 | E73 |
| | AGT-3 | E42 | GGT-3 | E74 |

```
                -continued
                |ATA-3    E43    |GTA-3    E75

|ATC-3    E44    |GTC-3    E76

|ATG-3    E45    |GTG-3    E77

|ATT-3    E46    |GTT-3    E78

|CAA-3    E47    |TAA-3    E79

|CAC-3    E48    |TAC-3    E80

|CAG-3    E49    |TAG-3    E81

|CAT-3    E50    |TAT-3    E82

|CCA-3    E51    |TCA-3    E83

|CCC-3    E52    |TCC-3    E84

|CCG-3    E53    |TCG-3    E85

|CCT-3    E54    |TCT-3    E86

|CGA-3    E55    |TGA-3    E87

|CGC-3    E56    |TGC-3    E88

|CGG-3    E57    |TGG-3    E89

|CGT-3    E58    |TGT-3    E90

|CTA-3    E59    |TTA-3    E91

|CTC-3    E60    |TTC-3    E92

|CTG-3    E61    |TTG-3    E93

|CTT-3    E62    |TTT-3    E94
```

The same coding is used for other enzymes, except that the letter E is replaced by a letter referring to a different restriction enzyme, such as M (MseI).

Next to this code, the name includes the size of the marker. For example, E14/M61-M873.6 is an AFLP marker that forms a band of about 863.6 base pairs with primers E14 and M61 in AFLP. It should be noted that we know from the prior art that the size of the marker can vary slightly with the method of detection used (radioactive versus fluorescent). On the basis of what has been said above, a person familiar with AFLP can reproduce these markers.

For the AFLP markers used here, the primer sequences are as follows, in the appropriate sequence list, with the 3' selective nucleotides being given after the vertical line:

```
E17: 5'-GAC TGC GTA CCA ATT C|CG-3'  (SEQ ID No. 1)

E24: 5'-GAC TGC GTA CCA ATT C|TC-3'  (SEQ ID No. 2)

E14: 5'-GAC TGC GTA CCA ATT C|AT-3'  (SEQ ID No. 3)

E19: 5'-GAC TGC GTA CCA ATT C|GA-3'  (SEQ ID No. 4)

E16: 5'-GAC TGC GTA CCA ATT C|CC-3'  (SEQ ID No. 5)

M54: 5'-GAT GAG TCC TGA GTA A|CCT-3' (SEQ ID No. 6)

M49: 5'-GAT GAG TCC TGA GTA A|CAG-3' (SEQ ID No. 7)

M61: 5'-GAT GAG TCC TGA GTA A|CTG-3' (SEQ ID No. 8)

M50: 5'-GAT GAG TCC TGA GTA A|CAT-3' (SEQ ID No. 9)

M47: 5'-GAT GAG TCC TGA GTA A|CAA-3' (SEQ ID No. 10)
```

A screening was carried out for the long cucumber, using the pooling strategy of bulked segregant analysis (BSA) to identify the markers coupled to the 4001 locus. We tested 256 different AFLP primer combinations on populations of doubled haploids and inbred lines of the 4001 plant. However, no closely coupled markers were identified in the long cucumber.

This was followed by marker identification for the 4001 type in a different background. The compact gene was localized on a single locus. We are dealing here with a monogenic characteristic or—though this is unlikely—with a number of closely coupled genes. For the fine mapping of the compact gene (the markers are at a short distance from the locus), a cucumber plant homozygous for the 4001 locus (homozygous compact) was crossed with a short cucumber plant. Since the genetic distance between the gherkin, the short cucumber and the long cucumber is relatively great, there are more markers present in the descendants of the hybrids formed between the long cucumber and the gherkin or the short cucumber in the region around the compact gene. We tested here 126 F2 individuals after hybridization-based introduction into the short cucumber background (self-pollination of an F1 plant from the hybridization of 4001 with Manar F1, which is a short cucumber type). 128 different AFLP primer combinations were used in the BSA screening. The markers identified in this project were further investigated by testing them on more individuals of the same population, namely on 632 F2 individuals (inbred F1 individuals from the hybridization of 4001 with Manar F1).

After this work, aimed at identifying the initial markers coupled to the 4001 locus, we screened a large population consisting of 4180 individuals, using 2 markers (TaqMan® SNP genotyping assay with a high throughput), which covered a region of about 12 cM with the 4001 gene in it. These markers are polymorphic between the long and the short cucumber and can be used, in the case of hybridization between the long and the short cucumber, for following the region with the 4001 gene (the compact gene) and for identifying recombinants for the fine mapping of the gene. We used two flanking co-dominant markers, i.e. markers that recognize both alleles (the wild-type and 4001) and which can therefore distinguish between plants with the 4001 gene in the heterozygous state and plants with the same gene in the homozygous state, the tests conducted being as follows:

MAS4: test with 1 flanking marker (derived from AFLP marker E23M49_M373.0):

```
                                     (primer MAS4-f, SEQ ID No. 11)
              GCATGCATGGACTGACTTACTAGA (primer MAS4-r, SEQ ID No. 12)
              GGAGACTCACATATCTTTCTGACACA
```

These two primers were used in PCR, where the following labelled samples were added:

```
VIC-CTAACTGCAAAAACAATGT
(this probe recognizes the normal type, which does
not contain the compact gene, and the heterozygous
compact plant type, SEQ ID No. 13),
and FAM-AACTGCAAAAGCAATGT
(this probe recognizes the heterozygous and the
homozygous compact plant type, SEQ ID No. 14).
```

MAS37: test with another flanking marker (derived from AFLP marker E23M80_M433.3):

```
                                    (primer MAS37-f, SEQ ID No. 15)
            AGGATCACCTGATGTTCAAGGAGTA (primer MAS37-r, SEQ ID No. 16)
            CGATGATACAGTTGGAAGGATGGA
```

These two primers were used in PCR, and the following labelled probes were added:

```
VIC-TATGGACGACTTTCATGTAG
(this probe recognizes the normal type (which
does not contain the compact gene) and the
heterozygous compact plant type, SEQ ID No. 17)
and FAM-TGGACGACTTTGATGTAG
(this probe recognizes the heterozygous and the
homozygous compact plant type, SEQ ID No. 18).
```

The detection was based on signals from the probes, as is well known from the prior art for this type of assay.

These tests indicate whether the DNA tested contained the DNA of homozygous wild-type, heterozygous compact type and homozygous compact type for either of the 2 markers that flank the compact gene. These assays were carried out according to the standard protocol of Applied Biosystems for the detection of recombinants (Taqman® SNP genotyping MGB assays, see e.g. www.appliedbiosystems.com).

The 491 identified recombinants were further investigated, and 137 individuals were found to exhibit recombination near the 4001 locus. This was followed by a bulked segregant analysis (BSA) on 4 pools with very small screening windows of 2.0 and 2.4 cM, respectievely, conducted to identify both cis (4001 type) and trans (normal type) coupled markers in the relevant domain. Altogether 512 EcoRI/MseI AFLP primer combinations were carried out on the 4 pools.

The candidate markers identified by the BSA method were mapped by determining the genotype of the 137 close recombinants for these markers.

All the scores, both the genotypical and the phenotypical ones, were verified on F3 individuals, from which F3 line scores were obtained, which gave an unambiguous F2 score. Verification of the phenotype was carried out on a selection of the 137 close recombinants. The selection consisted of 126 F3 plant lines. Phenotyping was conducted on 15 individuals for each F3 plant line. After the accurate location of the 4001 locus, the marker scores were verified on 64 F3 plant lines. For this purpose, 15 individuals were sown per line. Of these, the DNA was isolated, and the genotype of 15 individuals per F3 plant line was determined for the two high-throughput markers. After the analysis of the resulting genotypes, 4 individuals were selected per F3 plant line, where each genetic class was represented, i.e. the homozygous 4001, the heterozygous 4001, and the homozygous normal type. All the closely coupled EcoRI/MseI AFLP markers were tested on these 64×4 individuals, from which we could derive a reliable F2 genotype for the markers, so that the recombinations could be determined accurately.

For some of the markers 12 more individual plants of the F3 line were genotyped for these markers in order to obtain an unambiguous score.

The data obtained give a reliable genetic map of the 4001 locus, shown in FIG. 1. The location of the AFLP markers found indicates the 4001 locus (compact locus).

Flanking coupled markers were thus found with the aid of the AFLP method. The flanking marker E14/M61_M873.6 lies in this population at a distance of 0.05 cM from the compact locus, and the flanking marker E19/M50__M280.2 lies in this population at a distance of 0.67 cM from the compact locus. These markers are not polymorphic in the long cucumber.

Literature

Boonekamp (2006), *Groenten & Fruit* [=Fruit and Vegetables], Week 31, p. 19

"CPVO Protocol": Protocol for Distinctness, Uniformity and Stability Tests, Cucumber, *Cucumis sativus L.* European Union, Community Plant Variety Office, Boulevard Maréchal Foch, FR—49021, Angers Cedex 02. Document CPVO-TP/61/1, adopted on 27 Mar. 2002. Also available at http://www.cpvo.europa.eu, or from: http://www.cpvo.europa.eu/documents/TP/vegetales/TP_061_CUCUMIS_SATIVUS.pdf Gémes-Juhász, A. et al. (2002): "Effect of optimum stage of female gametophyte and heat treatment on in vitro gynogenesis induction in cucumber (*Cucumis sativus* L.)". *Plant Cell Reports*, 2002, vol. 21 (2), pp. 105-111

Goode et al. (1980): *Arkansas Farm Res.*, 29 (3), p. 4

Honkoop (2006), *Groenten & Fruit* [=Fruit and Vegetables], Week 38, pp. 6-7

Kauffman and Lower (1976), J. Americ. Soc. Hort. Sci. 101 (2): 150-151

Kubicki et al. (1986), Genetica Polonica, Vol 27 (3-4): 289-298

Scheffe, H (1953): "A Method for judging all contrasts in the Analysis of Variance". *Biometrika* (1953), 40 (1-2), pp. 87-110

Scheffe, H (1959): "The Analysis of Variance", John Wiley, New York

Schultheis et al. (1998): *Can. J. Plant Sci.*, 78, pp. 333-340 van Steekelenburg, N.A.M. (1986): Didymella bryoniae on glasshouse cucumbers. Dissertation, p. 105, Wageningen Agricultural University.

Vos, P. et al. (1995): "AFLP, a new technique for DNA fingerprinting", *Nucleic Acid Research*, 23 (21), pp. 4407-4414

Wehner et al. (1987): Cucurbit Genet. Coop. Rpt. 10, pp. 33-34.

TABLE 1

| | | | | Plant type | | | | | LSD | | Significant difference | | |
|---|---|---|---|---|---|---|---|---|---|---|---|---|---|
| CBP code | Obser. date | Obser. type | | Characteristic | Normal Value | Heterozygous compact Value | % of N | Homozygous compact Value | % of N | 0.5% | 0.1% | N/H | N/C | H/C |
| 2 | 17 Aug | M, cm | Plant | growth rate | 211.00 | 195.00 | 92 | 172.30 | 82 | 6.01 | 7.56 | ** | ** | ** |
| 3 | 29 Aug | M, cm | | Stem length at 15 internodes | 147.60 | 126.30 | 86 | 109.80 | 74 | 5.50 | 6.92 | ** | ** | ** |
| | 29 Aug | M, cm | | Length of lateral shoots | 82.20 | 66.50 | 81 | 37.40 | 45 | 9.86 | 12.40 | ** | ** | ** |
| | 29 Aug | M | | No. of lateral shoot internodes | 7.1 | 5.7 | 80 | 3.9 | 55 | 0.97 | 1.22 | ** | ** | ** |

TABLE 1-continued

| CBP code | Obser. date | Obser. type | | Characteristic | Plant type Normal Value | Heterozygous compact Value | Heterozygous compact % of N | Homozygous compact Value | Homozygous compact % of N | LSD 0.5% | LSD 0.1% | Significant difference N/H | Significant difference N/C | Significant difference H/C |
|---|---|---|---|---|---|---|---|---|---|---|---|---|---|---|
| | 8 Sept | M | | No. of lateral shoot internodes | 13.75 | 12.80 | 93 | 7.80 | 57 | 1.29 | 1.62 | NS | ** | ** |
| | 8 Aug | M, cm | Leaf | Length of leaf 1 | 40.93 | 36.30 | 89 | 24.13 | 59 | 2.40 | 2.82 | ** | ** | ** |
| | 8 Aug | M, cm | | Length of leaf 2 | 41.00 | 37.50 | 91 | 26.35 | 64 | 2.40 | 2.82 | ** | ** | ** |
| 10 | 8 Aug | M, cm | | Width of leaf 1 | 37.60 | 31.60 | 84 | 20.00 | 53 | 2.34 | 2.76 | ** | ** | ** |
| | 8 Aug | M, cm | | Width of leaf 2 | 38.40 | 33.23 | 87 | 21.83 | 57 | 2.34 | 2.76 | ** | ** | ** |
| | 8 Aug | C | | Length/width ratio | 1.08 | 1.14 | 106 | 1.21 | 112 | 0.023 | 0.029 | ** | ** | ** |
| 5 | 8 Aug | C, cm2 | | Blade area of leaf 1 | 771.45 | 577.56 | 75 | 242.61 | 31 | 73.00 | 85.97 | ** | ** | ** |
| | 8 Aug | C, cm2 | | Blade area of leaf 2 | 788.64 | 623.82 | 79 | 288.42 | 37 | 73.00 | 85.97 | ** | ** | ** |
| | 29 Aug | M, cm | | Length | 45.65 | 41.50 | 91 | 32.75 | 72 | 1.92 | 2.42 | ** | ** | ** |
| | 29 Aug | M, cm | | Width | 40.10 | 35.00 | 87 | 27.25 | 68 | 1.43 | 1.80 | ** | ** | ** |
| | 9 Aug | V | | Orientation | 3.4 | 4.5 | — | 7.3 | — | 0.47 | 0.59 | ** | ** | ** |
| 6 | 9 Aug | V | | Intensity of green colour | 4.5 | 6.5 | — | 7.6 | — | 0.46 | 0.57 | ** | ** | ** |
| 7 | 9 Aug | V | | Bumpiness | 5.5 | 7.5 | — | 7.2 | — | 0.46 | 0.58 | ** | ** | NS |
| | 8 Sept | V | | Brittleness | 5.0 | 8.0 | — | 7.0 | — | | | | | |
| | 18 Aug | M, cm | Flower | Length of petal 1 | 4.18 | 3.34 | 80 | 3.04 | 73 | 0.33 | 0.39 | ** | ** | NS |
| | 18 Aug | M, cm | | Length of petal 2 | 4.11 | 3.38 | 82 | 2.95 | 72 | 0.33 | 0.39 | ** | ** | ** |
| | 18 Aug | M, cm | | Width of petal 1 | 2.77 | 2.09 | 75 | 1.75 | 63 | 0.24 | 0.29 | ** | ** | ** |
| | 18 Aug | M, cm | | Width of petal 2 | 2.85 | 2.11 | 74 | 1.77 | 62 | 0.24 | 0.29 | ** | ** | ** |
| | 18 Aug | C | | Petal length/width ratio | 1.45 | 1.62 | 112 | 1.70 | 117 | | | | | |
| | 29 Aug | M, g | Fruit | Weight | 372.88 | 255.50 | 95 | 299.58 | 80 | | | NS | ** | ** |
| 19 | 29 Aug | M, cm | | Length | 30.95 | 27.65 | 89 | 25.00 | 81 | | | ** | ** | ** |

TABLE 2

| CPB code | Obs. type | | Characteristics | Plant type Normal (long) | Short | Gherkin | Homozygous compact | Overlap |
|---|---|---|---|---|---|---|---|---|
| 2 | v | Plant | growth rate | 6 | 5-6 | 4-5 | 3 | |
| 3 | v | | Length of stem at 15 internodes | 7 | 4-5 | 3-5 | 3 | C/G |
| | v | | Length of side shoots | 7 | 1-7 | 1-6 | 3 | C/G, C/Sh |
| | v | | No. of side-shoot internodes | 7 | 1-7 | 1-6 | 3 | C/G, C/Sh |
| | v | | | | | | | |
| | V | Leaf | Lobe-to-tip length | 7 | 4-6 | 4-5 | 3 | |
| 10 | V | | Width | 5-7 | 4-6 | 4-5 | 3 | |
| 5 | V | | Leaf blade area | 7 | 4-6 | 4-5 | 3 | |
| | V | | Stalk-to-tip length | 7 | 4-6 | 4-5 | 3 | |
| | V | | Brittleness | 5 | 5 | 6 | 7 | |
| | V | | Orientation | 3 | 3-5 | 4-7 | 7 | C/G |
| 6 | V | | Intensity of green colour | 3-5 | 3-5 | 4-6 | 9 | |
| 7 | V | | "Bumpiness" | 3-5 | 3-5 | 3-6 | 7 | |
| | V | Flower | Length of petals | 7 | 4-6 | 3-5 | 3 | C/G |
| | V | | Width of petals | 7 | 4-6 | 3-5 | 3 | C/G |
| | V | Fruit | Weight | 7 | 1-3 | 1-2 | 3 | C/Sh |
| 19 | V | | Length | 7 | 1-2 | 1-2 | 3 | |
| | | | Varieties used as examples | Sabrina Korinda | Alamir Turbulence | Capra Delphina | | |

The invention claimed is:

1. A cucumber plant (*Cucumis sativus*) whose genome comprises a compact gene, obtainable from seeds deposited under Accession number NCIMB 41266, in homozygous or heterozygous form which expresses a combination of the following phenotypical characteristics: shorter lateral shoots, shorter internodes, smaller leaves, smaller flowers and shorter fruits as compared to the usual cucumber plant type lacking the compact gene and, in case of plants comprising the compact gene in homozygous form, as compared to plants comprising a compact gene in heterozygous form, and wherein the presence of the compact gene can be demonstrated by hybridizing said cucumber plant with a gherkin or short cucumber plant, and by analyzing the F1 plants obtained by this hybridization using an AFLP method and at least one of the following markers: SEQ ID NO: 3 and SEQ ID NO: 8 forming a band of about 873.6 base pairs; SEQ ID NO: 4 and SEQ ID NO: 9 forming a band of about 280.2 base pairs; SEQ ID NO: 2 and SEQ ID NO: 7 forming a band of about 211.5 base pairs; SEQ ID NO: 1 and SEQ ID NO: 6 forming a band of about 179.0 base pairs; SEQ ID NO: 5 and SEQ ID NO: 10 forming a band of about 426.1 base pairs; SEQ ID NO: 5 and SEQ ID NO: 10 forming a band of about 411.0 base pairs; or SEQ ID NO: 5 and SEQ ID NO: 10 forming a band of about 402.9 base pairs, and wherein said cucumber plant does not contain the Little Leaf locus (ll) present in the Arkansas Little leaf type.

2. The plant of claim 1, wherein said plant comprises a main stem length at 15 internodes, as measured from the substrate, of more than 50 cm.

3. The plant according to claim 1, wherein said plant is indeterminate.

4. The plant according to claim 1, wherein said plant is a long cucumber type.

5. The plant of claim 1, wherein the expression of the compact gene in plants that are homozygous for the compact gene exhibit a combination of the following phenotypical characteristics: (a) the area of the blade of the tenth true leaf in plants with the compact gene 39 days after sowing is at most 50% of the leaf blade area of plants of the usual cucumber type 39 days after sowing, (b) the maximum width of the petals 39 days after sowing the plants with the compact gene is at most 75% of the maximum width of the petals of plants of the usual cucumber type 39 days after sowing, (c) the length of the lateral shoots 56 days after sowing the plants with the compact gene is at most 60% of the length of the lateral shoots 56 days after sowing plants of the usual cucumber type, and (d) the number of internodes on the lateral shoots 56 days after sowing the plants with the compact gene is at most 70% of the number of internodes on the lateral shoots 56 days after sowing plants of the usual cucumber type.

6. The plant of claim 1, wherein said plant comprises the compact gene in heterozygous form, which produces a segregating population after self-fertilization having the following proportions: about 25% of the plants are plants with the normal phenotypic characteristics of a plant lacking the compact gene, about 50% are plants with intermediate compact characteristics and about 25% are plants with homozygous compact characteristics.

7. The plant of claim 1, wherein the plants of the usual cucumber type are plants of the Korinda or Sabrina type.

8. The plant of claim 1, wherein the plant comprises a compact gene in homozygous form and is a doubled haploid plant.

9. The plant of claim 1, wherein said plants homozygous for a compact gene are derived from the seeds deposited under NCIMB number 41266.

10. The plant of claim 1, wherein the compact gene is the gene that is flanked by the AFLP markers E14/M61$_{13}$ M873.6 and E19/M50$_{13}$ M280.2 in the case of hybridization of plants grown from the seeds deposited under NCIMB number 41266 with a short cucumber or gherkin.

11. Seeds, cells, or tissues of the plant of claim 1 comprising the compact gene in their genome.

12. The plant of claim 1, wherein said plant is a hybrid plant comprising a compact gene in heterozygous form and expresses intermediate compact characteristics.

13. Cells, fruits or seeds of the hybrid plant of claim 12, wherein said plant comprises the compact gene.

14. The plant of claim 1, wherein the compact gene is flanked by AFLP marker E14/M61-M873.6 and/or E19/M50-M280.2 in crosses of plants derived from reference seed deposited at NCIMB under accession number 41266 with the short cucumber or gherkin plants, and wherein said gene segregates with all the above phenotypical characteristics in a monogenic intermediate manner in the F2 progeny of said crosses.

15. The plant of claim 1, wherein the cucumber plant type lacking a compact gene is Korinda.

16. The plant of claim 14, wherein the short cucumber or gherkin plant is Manar F1.

17. The plant of claim 2, said plant comprises a main stem length at 15 internodes, as measured from the substrate, of more than 80 cm.

18. The plant of claim 7, wherein said cucumber plants lacking a compact gene are of the Korinda type and are obtained from seeds deposited under NCIMB Accession number 41585.

* * * * *

UNITED STATES PATENT AND TRADEMARK OFFICE
CERTIFICATE OF CORRECTION

PATENT NO. : 8,710,303 B2  Page 1 of 1
APPLICATION NO. : 12/741772
DATED : April 29, 2014
INVENTOR(S) : Crienen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this
Twenty-ninth Day of September, 2015

Michelle K. Lee
*Director of the United States Patent and Trademark Office*